US009724425B2

(12) United States Patent
Amrein et al.

(10) Patent No.: US 9,724,425 B2
(45) Date of Patent: Aug. 8, 2017

(54) CONJUGATES OF INSULIN-LIKE GROWTH FACTOR-1 AND POLY(ETHYLENE GLYCOL)

(71) Applicants: Hoffmann-La Roche Inc., Little Falls, NJ (US); Kerstin Kruger, Tutzing (DE)

(72) Inventors: Beat Amrein, Ruenenberg (CH); Stefan Foser, Steinhausen (CH); Kurt Lang, Penzberg (DE); Friedrich Metzger, Freiburg (DE); Joerg Thomas Regula, Munich (DE); Andreas Schaubmar, Penzberg (DE); Friederike Hesse, Munich (DE); Klaus-Peter Kuenkele, Marzling (DE); Martin Lanzendoerfer, Tutzing (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/482,703

(22) Filed: Sep. 10, 2014

(65) Prior Publication Data
US 2015/0099699 A1  Apr. 9, 2015

Related U.S. Application Data

(63) Continuation of application No. 13/845,179, filed on Mar. 18, 2013, now abandoned, which is a continuation of application No. 13/551,648, filed on Jul. 18, 2012, now abandoned, which is a continuation of application No. 12/791,904, filed on Jun. 2, 2010, now abandoned, which is a continuation of application No. 11/825,827, filed on Jul. 9, 2007, now abandoned, which is a continuation of application No. 11/313,101, filed on Dec. 20, 2005, now abandoned.

(30) Foreign Application Priority Data

Dec. 22, 2004  (EP) ..................... 04030415

(51) Int. Cl.
C07K 4/00 (2006.01)
C07K 14/00 (2006.01)
A61K 38/00 (2006.01)
A61K 38/18 (2006.01)
C07K 14/475 (2006.01)
C07K 14/48 (2006.01)
A61K 47/48 (2006.01)
C07K 14/65 (2006.01)

(52) U.S. Cl.
CPC ...... *A61K 47/48215* (2013.01); *C07K 14/475* (2013.01); *C07K 14/65* (2013.01)

(58) Field of Classification Search
CPC .... C07K 14/475; C07K 14/65; C07K 14/575; A61K 38/00; A61K 47/48215; A61K 2039/6031
See application file for complete search history.

(56) References Cited

U.S. PATENT DOCUMENTS

| 4,904,584 | A | 2/1990 | Shaw |
| 5,672,662 | A | 9/1997 | Harris et al. |
| 5,681,814 | A | 10/1997 | Clark et al. |
| 5,714,460 | A | 2/1998 | Gluckman et al. |
| 5,861,373 | A | 1/1999 | Gluckman et al. |
| 5,932,462 | A | 8/1999 | Harris et al. |
| 6,403,764 | B1 * | 6/2002 | Dubaquie ............. C07K 14/65 530/300 |
| 6,506,874 | B1 | 1/2003 | Dubaquie et al. |
| 6,509,443 | B1 | 1/2003 | Dubaquie et al. |
| 6,559,122 | B1 | 5/2003 | Oeswein et al. |
| 6,623,950 | B1 | 9/2003 | von der Osten et al. |
| 7,431,921 | B2 | 10/2008 | Rasmussen et al. |
| 7,662,933 | B2 | 2/2010 | Kinstler et al. |
| 2003/0023049 | A1 | 1/2003 | Pettit |
| 2003/0109427 | A1 | 6/2003 | Shirley et al. |
| 2004/0014652 | A1 | 1/2004 | Trouet et al. |
| 2006/0074011 | A1 | 4/2006 | Shirley et al. |
| 2009/0253628 | A1 | 10/2009 | Holtmann et al. |

FOREIGN PATENT DOCUMENTS

| DE | 3924705 | 1/1991 |
| EP | 0123228 | 10/1984 |
| EP | 0128733 | 12/1984 |
| EP | 0400472 | 12/1990 |

(Continued)

OTHER PUBLICATIONS

Robinson et al. Biochemistry 2004, 43: 11533-11545.*
Kinstler et al. Adv. Drug. Del. Rev. 2002. 54: 477-485.*
Brzozowski et al. Biochemistry 2002. 41: 9389-9397.*
Bouc et al., "Complete characterization of the human IGF-I nucleotide sequence isolated from a newly constructed adult liver cDNA library", FEBS Lett, 196(1):108-112 (1986).
Brzozowski et al., "Structural origins of the functional divergence of human insulin-like growth factor-I and insulin", Biochem, 41(30):9389-9397 (2002).
Burgess et al., "Possible dissociation of the heparin-binding and mitogenic activities of heparin-binding (acidic fibroblast) growth factor-1 from its receptor-binding activities by site-directed mutagenesis of a single lysine residue", J Cell Biol., 111(5 Pt 1):2129-2138 (1990).
Carro et al., "Serum insulin-like growth factor I regulates brain amyloid-beta levels", Nat. Med, 8(12):1390-1397 (2002).

(Continued)

*Primary Examiner* — Chang-Yu Wang
(74) *Attorney, Agent, or Firm* — Jones Day

(57) ABSTRACT

A conjugate consisting of an insulin-like growth factor-1 (IGF-I) variant and one or two poly(ethylene glycol) group(s), characterized in that said IGF-I variant has an amino acid alteration at up to three amino acid positions 27, 37, 65, 68 of the wild-type IGF-I amino acid sequence so that one or two of said amino acids is/are lysine and amino acid 27 is a polar amino acid but not lysine, is conjugated via the primary amino group(s) of said lysine(s) and said poly(ethylene glycol) group(s) have an overall molecular weight of from 20 to 100 kDa is disclosed. This conjugate is useful for the treatment of neurodegenerative disorders like Alzheimer's Disease.

6 Claims, 10 Drawing Sheets

(56) References Cited

FOREIGN PATENT DOCUMENTS

| EP | 0473084 | | 3/1992 | |
|---|---|---|---|---|
| EP | 0597033 | | 5/1994 | |
| WO | WO8905822 | * | 6/1989 | ............ C07K 7/10 |
| WO | 93/02695 | | 2/1993 | |
| WO | 94/12219 | | 6/1994 | |
| WO | WO95/32003 | * | 5/1995 | ............ A61K 47/48 |
| WO | 95/32003 | | 11/1995 | |
| WO | 99/55362 | | 11/1999 | |
| WO | 99/62536 | | 12/1999 | |
| WO | 01/91798 | | 12/2001 | |
| WO | 02/32449 | | 4/2002 | |
| WO | 2004/060300 | | 7/2004 | |
| WO | WO2004/060300 | * | 7/2004 | |
| WO | 2006/066891 | | 6/2006 | |
| WO | 2008/025528 | | 3/2008 | |
| WO | 2009/121759 | | 10/2009 | |

OTHER PUBLICATIONS

Carro et al., "The role of insulin and insulin-like growth factor I in the molecular and cellular mechanisms underlying the pathology of Alzheimer's disease", Eur J Pharmacol, 490(1-3):127-133 (2004).
De Pagter-Holthuizen et al., "Organization of the human genes for insulin-like growth factors I and II", FEBS Letl, 195(1-2):179-184 (1986).
Duguay et al., "Mutational analysis of the insulin-like growth factor I prohormone processing site", J. Biol Chem., 270 (29):17566-17574 (1995).
Duncan et al., "A new reagent which may be used to introduce sulfhydryl groups into proteins, and its use in the preparation of conjugates for immunoassay", Anal. Biochem. 132(1):68-73 (1983).
Esposito et al., "PEGylation of growth hormone-releasing hormone (GRF) analogues", Advanced Drug Delivery Review, 55(10):1279-1291 (2003).
Foser et al., "Improved biological and transcriptional activity of monopegylated interferon-alpha-2a isomers", Pharmacogenomics J., 3(6):312-319 (2003).
Fowlkes et al., "Insulin-like growth factor (IGF)-binding protein-3 (IGFBP-3) functions as an IGF-reversible inhibitor of IGFBP-4 proteolysis", J Biol Chem., 270(46):27481-27488 (1995).
Grassetti et al., "Determination of sulfhydryl groups with 2,2'- or 4,4'-dithiodipyridine", Arch Biochem Biophys, 119 (1):41-49 (1967).
Greenwald, "PEG drugs: an overview", J Control Release, 74(1-3):159-171 (2001).
Harris et al., "Pegylation: a novel process for modifying pharmacokinetics", Clin. Pharmacokinelic, 40(7):539-551 (2001).
Hermanson, Bioconjugate Techniques, Academic Press, San Diego, 147-148 (1996).
International Search Report for PCT/EP2010/00174—Mar. 8, 2011.
Japanese Laid-open Patent (Kohyo) Publication No. Hei 10-500693 (1998).
Japanese Laid-open Patent (Kohyo) Publication No. Hei 6-506095 (1996).
Kiefer et al., "Molecular cloning of a new human insulin-like growth factor binding protein", Biochem. Biophys Res Commun, 176(1):219-225 (1991).
Kim et al., "Pegylated recombinant human epidermal growth factor (rhEGF) for sustained release from biodegradable PLGA microspheres", Biomaterials, 23(11):2311-2317 (2002).
Kinstler et al., "Mono-N-terminal poly(ethylene glycol)-protein conjugates", Adv Drug Deliv Rev., 54(4):477-485 (2002).
March, "Advanced Organic Chemistry", 375-376 (1977).
Metzger et al., "Separation of Fast from Slow Anabolism by Site—specific PEGylation of Insulin-like Growth Factor! (IGF-I)", J. Biol. Chem., 286(22):19501-19510 (2011).
Monfardini et al., "A branched monomethoxypoly(ethylene glycol) for protein modification", J. Bioconjugate Chem., 6(1):62-69 (1995).
Morpurgo et al., "Preparation of characterization of poly(ethylene glycol) vinyl sulfone", Bioconjug Chem., 7 (3):363-368 (1996).
Park et al., "Preparation and characterization of mono-PEGylated epidermal growth factor: evaluation of in vitro biologic activity", Pharm Res., 19(6):845-851 (2002).
Pawson et al., "Assembly of cell regulatory systems through protein interaction domains", Science, 300 (5618):445-452 (2003).
Richards et al., "PS2APP transgenic mice, coexpressing hPS2mut and hAPPswe, show age-related cognitive deficits associated with discrete brain amyloid deposition and inflammation", J. Neuroscience, 23(26):8989-9003 (2003).
Robinson et al., "Synthesis and characterization of biotinylated forms of insulin-like growth factor-1: topographical evaluation of the IGF-1/IGFBP-2 and IGFBP-3 interface", Biochem, 43(36):11533-11545 (2004).
Sandberg-Nordgvist et al., "Characterization of two cDNAs encoding insulin-like growth factor 1 (IGF-1) in the human fetal brain", Brain Res Mol Brain Res.,12(1-3):275-277 (1992).
Shimasaki et al., "Molecular cloning of the cDNAs encoding a novel insulin-like growth factor-binding protein from rat and human", Mol. Endocrinol, 4(10):1451-1458 (1990).
Singh et al., "Insulin-like growth factor (IGF)-binding protein-3 (IGFBP-3) functions as an IGF-reversible inhibitor of IGFBP-4 proteolysis", J Biol Chem, 207(46):27481-27488 (1995).
Steenbergh et al., "Complete nucleotide sequence of the high molecular weight human IGF-I mRNA", Biochem Biophys. Res. Commun., 175(2):507-514 (1991).
Tanner et al., "Comparative rapidity of response of height, limb muscle and limb fat to treatment with human growth hormone in patients with and without growth hormone deficiency", Acta Endocrinol (Copenh), 84(4):681-696 (1977).
Uthne et al., "Effects of human somatomedin preparations on membrane transport and protein synthesis in the isolated rat diaphragm", J. Clin Endocrinol Metab, 39(3):548-554 (1974).
Veronese et al., J. Bioactive and Compatible Polymers 12:196-207 (1997).
Veronese, "Peptide and protein PEGylation: a review of problems and solutions", Biomaterials, 22(5):405-417 (2001).

* cited by examiner

| Compound | $EC_{50}$ [nM] | $B_{Max}$ [Ratio] | $n_H$ |
|---|---|---|---|
| rhIGF-I | 6.3 ± 1.1 | 5.1 ± 0.4 | 2.27 ± 0.65 |
| Peak 1 | 91.5 ± 215.0 | 8.2 ± 6.6 | 0.34 ± 0.31 |
| Peak 2 | 13.4 ± 2.7 | 5.5 ± 0.4 | 1.27 ± 0.30 |
| Peak 3 | 21.5 ± 4.9 | 5.5 ± 0.5 | 1.19 ± 0.31 |
| Mix | 28.8 ± 5.5 | 5.3 ± 0.4 | 1.28 ± 0.29 |
| Des(1-3) Peak 3 | 10.8 ± 3.7 | 6.0 ± 1.0 | 1.08 ± 0.41 |

SEQUENCE LISTING

<160> NUMBER OF SEQ ID NOS: 11

<210> SEQ ID NO 1
<211> LENGTH: 105
<212> TYPE: PRT
<213> ORGANISM: Homo sapiens

<400> SEQUENCE: 1

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met
            100                 105

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Leu Arg Arg Leu
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 3

Asp Glu Cys Cys Phe Arg Ser Cys
  1               5

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Met Tyr Cys Ala Pro Leu Lys Pro Ala Lys Ser Ala
  1               5                  10

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Arg Gly Phe Tyr Phe Asn Lys Pro Thr Gly Tyr Gly Ser Ser Ser
  1               5                  10                  15

Arg Arg Ala Pro Gln Thr Gly Ile Val
             20                  25

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Pro Glu Thr Leu Cys Gly Ala Glu Leu Val
  1               5                  10

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ala Leu Gln Phe Val Cys Gly
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Arg Gly Phe Tyr Phe Asn
  1               5
```

```
<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Thr Gly Tyr Gly Ser Ser Ser Arg Arg Ala Pro Gln Thr
  1               5                  10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Ala Lys Ser Ala
  1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Pro Leu Lys Pro Ala
  1               5
```

CONJUGATES OF INSULIN-LIKE GROWTH FACTOR-1 AND POLY(ETHYLENE GLYCOL)

PRIORITY TO RELATED APPLICATIONS

This application is a continuation of U.S. application Ser. No. 13/845,179, filed Mar. 18, 2013, now pending, which is a continuation of U.S. application Ser. No. 13/551,648, filed Jul. 18, 2012, now abandoned, which is a continuation of U.S. application Ser. No. 12/791,904, filed Jun. 2, 2010, now abandoned; which is a continuation of U.S. application Ser. No. 11/825,827, filed Jul. 9, 2007, now abandoned; which is a continuation of U.S. application Ser. No. 11/313,101, filed Dec. 20, 2005, now abandoned; which claims the benefit of European Application No. 04030415.6, filed Dec. 22, 2004. The entire contents of the above-identified applications are hereby incorporated by reference.

FIELD OF THE INVENTION

This invention relates to conjugates of insulin-like growth factor-I (IGF-I) with poly(ethylene glycol) (PEG), pharmaceutical compositions containing such conjugates, and methods for the production and methods of use of such conjugates.

BACKGROUND OF THE INVENTION

Alzheimer's disease (AD) is an increasingly prevalent form of neurodegeneration that accounts for approximately 50%-60% of the overall cases of dementia among people over 65 years of age. Death of pyramidal neurons and loss of neuronal synapses in brains regions associated with higher mental functions results in the typical symptoms, characterized by gross and progressive impairment of cognitive function. Neuropathologically, the major hallmarks of AD are the presence of two characteristic lesions: the amyloid senile plaque and neurofibrillary tangle (NFT). While the plaque is deposited extraneuronally, the tangle is observed intraneuronally in the post-mortem brain. One of the major components of the amyloid plaque core is the pathologically deposited small amyloid-beta-peptide (Aβ), which is cleaved by secretases from amyloid precursor protein (APP). Aβ, a self-aggregating peptide of 39-43 residues (MW~4 kDa), is synthesized as part of the larger APP (110-120 kDa). APP is a type I integral membrane glycoprotein with a large N-terminal extracellular domain, a single transmembrane domain and a short cytoplasmic tail. The Aβ region spans portions of the extracellular and transmembrane domains of APP. The most common hypothesis for the participation of APP in neuronal cell death in AD is the amyloid hypothesis. This hypothesis postulates that plaque amyloid depositions or partially aggregated soluble AB trigger a neurotoxic cascade, thereby causing neurodegeneration similar to AD pathology.

Insulin-like growth factor I (IGF-I) is a circulating hormone structurally related to insulin. IGF-I was traditionally considered the major mediator of the actions of growth hormone on peripheral tissues IGF-I consists of 70 amino acids and is also named somatomedin C and defined by SwissProt No. P01343. Use, activity and production are mentioned in, e.g., EP 0 123 228; EP 0 128 733; U.S. Pat. No. 5,861,373; U.S. Pat. No. 5,714,460; EP 0 597 033; WO 02/32449; WO 93/02695.

The regulation of IGF-I function is quite complex. In the circulation, only 0.2% of IGF-I exists in the free form whereas the majority is bound to IGF-binding proteins (IGFBP's), which have very high affinities to IGF's and modulate IGF-I function. The factor can be locally liberated by mechanisms releasing IGF-I such as proteolysis of IGFBPs by proteases.

IGF-I plays a paracrine role in the developing and mature brain, and in vitro studies indicate that IGF-I is a potent non-selective trophic agent for several types of neurons in the CNS.

Reduction of brain and serum levels of free IGF-I has been related to the pathogenesis of sporadic and familial forms of AD. Furthermore, IGF-I protects neurons against Aβ-induced neurotoxicity. Peripherally administered IGF-I is capable of reducing brain Aβ levels in rats and mice and that in a transgenic AD mouse model prolonged IGF-I treatment significantly reduced brain amyloid plaque load. These data strongly support the idea that IGF-I is able to reduce brain Aβ levels and plaque-associated brain dementia by clearing Aβ from the brain.

Covalent modification of proteins with poly(ethylene glycol) (PEG) has proven to be a useful method to extend the circulating half-lives of proteins in the body. Other advantages of PEGylation are an increase of solubility and a decrease in protein immunogenicity. A common method for the PEGylation of proteins is the use of poly(ethylene glycol) activated with amino-reactive reagents like N-hydroxysuccinimide (NHS). With such reagents poly(ethylene glycol) is attached to the proteins at free primary amino groups such as the N-terminal α-amino group and the ε-amino groups of lysine residues. However, a major limitation of this approach is that proteins typically contain a considerable amount of lysine residues and therefore the poly(ethylene glycol) groups are attached to the protein in a non-specific manner at all of the free ε-amino groups, resulting in a heterologous product mixture of random PEGylated proteins. Therefore, many NHS-PEGylated proteins are unsuitable for commercial use because of low specific activity. Inactivation results from covalent modification of one or more lysine residues or the N-terminal amino residue required for biological activity or from covalent attachment of the poly(ethylene glycol) residues near or at the active site of the protein.

WO 94/12219 and WO 95/32003 claim polyethylene glycol conjugates comprising PEG and IGF or a cysteine-mutated IGF, where the PEG is attached to said mutein at a free cysteine in the N-terminal region of the mutein. WO 2004/60300 describes N-terminally PEGylated IGF-I.

SUMMARY OF THE INVENTION

The invention comprises an IGF-I variant having an amino acid alteration at at least one of amino acid positions 27, 37, 65 and 68 of the wild-type IGF-I amino acid sequence so that one or more of amino acids 37, 65, 68 is/are lysine (K) and amino acid 27 is a polar amino acid but not lysine.

Amino acid 27 can be, for example, arginine.

Such IGF-I variants are useful as intermediates (IGF-I intermediates) for the production of lysine-PEGylated IGF-I.

It has surprisingly been found that a lysine-PEGylated IGF-I variant (amino-reactive PEGylated IGF-I variant), preferably a 20 kDa to 100 kDa lysine-PEGylated IGF-I variant, and especially preferably a lysine-monoPEGylated IGF-I variant, has superior properties in regard to therapeutic applicability.

A further embodiment of the invention is a composition containing, inter alfa, both a lysine-PEGylated IGF-I variant according to the invention and an IGF-I variant which is N-terminally PEGylated. The molecular ratio can be, for example, within the range of 9:1 to 1:9, such as a composition wherein the molar ratio is at least 1:1 (at least one part lysine-PEGylated IGF-I variant per one part of N-terminally PEGylated IGF-I variant), for example at least 6:4 (at least six parts lysine-PEGylated IGF-I variant per four parts of N-terminally PEGylated IGF-I variant). The lysine-PEGylated IGF-I variant and the N-terminally PEGylated IGF-I variant may be monoPEGylated. The variant may be identical in both the lysine-PEGylated IGF-I variant and the N-terminally PEGylated IGF-I variant. The variant may be selected from the group consisting of RRKK, RRKR, RRRK, RKRR. PEG may typically have an average molecular weight of 30 to 45 kDa, especially 30 kDa or 40 kDa. Lysine-PEGylated IGF-I variant and N-terminally PEGylated IGF-I variant show comparable affinities in binding of IGF binding proteins (e.g. BP4 and BP5), but different activities in regard to IGF-IR phosphorylation.

The present invention provides a conjugate containing an IGF-I variant and poly(ethylene glycol) group(s), where the IGF-I variant has amino acid alteration(s) at at least one of amino acid positions 27, 37, 65 and 68 of the wild-type IGF-I amino acid sequence so that one or more of amino acids 37, 65, 68 is/are lysine (K), amino acid 27 is a polar amino acid but not lysine and said PEG is conjugated to said IGF-I variant via primary amino group(s), typically via primary amino group(s) of lysine(s).

In general, the poly(ethylene glycol) group(s) may have an overall molecular weight of at least 20 kDa, such as from about 20 to 100 kDa or such as from 20 to 80 kDa.

The poly(ethylene glycol) group(s) may be conjugated to the IGF-I variant via the primary amino group(s) of lysine at one or more amino acid positions 37, 65, 68 (amino-reactive PEGylation) and are optionally PEGylated at the N-terminal amino acid. The conjugate may be mono- or diPEGylated at lysine residue(s) at one or more amino acid position(s) 37, 65, 68 and optionally PEGylated at the N-terminal amino acid. Thus, the conjugate may be monoPEGylated at K65, K68, or K37 or diPEGylated at K65 and K68 and optionally PEGylated at the N-terminal amino acid. Preferably not more than 20% of the PEGylated IGF-I variant is additionally N-terminal PEGylated.

IGF-I variants are designated herein as follows: K65 means that amino acid 65 is lysine, R27 means that amino acid 27 is arginine etc. An IGF-I variant bearing the amino acids R27, K37, K65, K68 is designated RKKK. IGF-I wildtype is designated KRKK.

Particular IGF-I variants and variants in the conjugates may be, for example, RRKK, RRKR, RRRK, RKRR.

In another embodiment, the (PEGylated) IGF-I variant according to the invention may be a variant in which up to three (preferably all three) amino acids at the N-terminus are truncated. The respective wild type mutant is named Des(1-3)-IGF-I and lacks the amino acid residues gly, pro and glu from the N-terminal.

The poly(ethylene glycol) group(s) may be either linear or branched.

The invention further comprises methods for the preparation of a conjugate according to the invention using the IGF-I intermediates. The method comprises the preparation of a conjugate comprising an IGF-I variant and one or two poly(ethylene glycol) group(s), where the poly(ethylene glycol) group(s) may have an overall molecular weight of at least 20 kDa, or from about 20 to 100 kDa, or from 20 to 80 kDa, by reacting the IGF-I intermediate with activated (polyethylene) glycol under conditions such that the (poly-ethylene) glycol is chemically bound to the IGF-I intermediate via primary lysine amino group(s) of IGF-I variant.

The invention further comprises pharmaceutical compositions containing a conjugate according to the invention, which may also include a pharmaceutically acceptable carrier.

The invention further comprises methods for the production of pharmaceutical compositions containing a conjugate according to the invention.

The invention further comprises methods for the treatment of AD, comprising the administration of a pharmaceutically effective amount of amino-reactive PEGylated IGF-I variant to a patient in need of such treatment, in, for example, one to two applications per week.

BRIEF DESCRIPTION OF THE FIGURES

FIG. 6: Quantitative analysis of IGF-IR phosphorylation in NIH-3T3 Cells. Dose response curves obtained form the experiments in Example 7 were fitted with one-site binding kinetics to obtain specific binding ($B_{Max}$), halfmaximal binding concentrations ($EC_{50}$) and Hill coefficients ($n_H$). Data represent means±SEM of 6 measurements from 3 independent cultures.

DETAILED DESCRIPTION OF THE INVENTION

Figure 1:
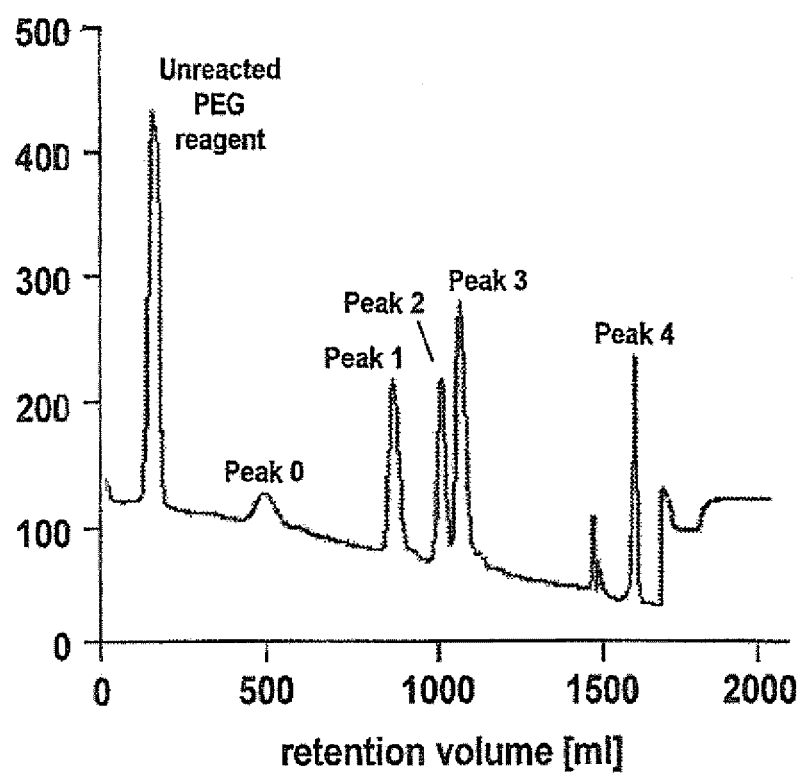
FIG. 1: IEC-HPLC of PEG-IGF. Pure positional isomers were separated from the PEGylation mixture using a preparative strong-cation exchange column (TOSOH-BIOSEP, SP-5PW). Five different peak fractions (numbered 0-4) were isolated and processed for further analysis.

"PEGylated IGF-I variant" or "amino-reactive PEGylation" as used herein means an IGF-I variant that is covalently bonded to one or two poly(ethylene glycol) groups by amino-reactive coupling to one or two lysines of the IGF-I variant molecule. The PEG group(s) is/are attached at the sites of the IGF-I variant molecule that are the primary ε-amino groups of the lysine side chains. It is further possible that PEGylation occurs in addition on the N-terminal α-amino group. Due to the synthesis method and variant used, PEGylated IGF-I variant can consist of a mixture of IGF-I variants, PEGylated at K65, K68 and/or K37 with or without N-terminal PEGylation, whereby the sites of PEGylation can be different in different molecules or can be substantially homogeneous in regard to the amount of poly (ethylene glycol) side chains per molecule and/or the site of PEGylation in the molecule. Preferably the IGF-I variants are mono- and/or diPEGylated and especially purified from N-terminal PEGylated IGF-I variants.

Amino-reactive PEGylation as used herein designates a method of randomly attaching polyethylene glycol) chains to primary lysine amino group(s) of the IGF-I variant by the use of reactive (activated) poly(ethylene glycol), preferably by the use of N-hydroxysuccinimidyl esters of, preferably, methoxypoly(ethylene glycol). The coupling reaction attaches poly(ethylene glycol) to reactive primary ε-amino groups of lysine residues and optionally the α-amino group of the N-terminal amino acid of IGF-I. Such amino group conjugation of PEG to proteins is well known in the art. For example, review of such methods is given by Veronese, F. M. Biomaterials 22 (2001) 405-417. According to Veronese, the conjugation of PEG to primary amino groups of proteins can be performed by using activated PEGs which perform an alkylation of said primary amino groups. For such a reaction, activated alkylating PEGs, for example PEG aldehyde, PEG-tresyl chloride or PEG epoxide can be used. Further useful reagents are acylating PEGs such as hydroxysuccinimidyl esters of carboxylated PEGs or PEGs in which the terminal hydroxy group is activated by chloroformates or carbonylimidazole. Further useful PEG reagents are PEGs with amino acid arms. Such reagents can contain the so-called branched PEGs, whereby at least two identical or different PEG molecules are linked together by a peptidic spacer (preferably lysine) and, for example, bound to IGF-I variant as activated carboxylate of the lysine spacer. Mono-N-terminal coupling is also described by Kinstler, O., et al., Adv. Drug Deliv. Rev. 54 (2002) 477-485.

"PEG or poly(ethylene glycol)" as used herein means a water soluble polymer that is commercially available or can be prepared by ring-opening polymerization of ethylene glycol according to methods well known in the art. The term "PEG" is used broadly to encompass any polyethylene glycol molecule, wherein the number of ethylene glycol units is at least 460, preferably 460 to 2300 and especially preferably 460 to 1840 (230 PEG units refers to an molecular weight of about 10 kDa). The upper number of PEG units is only limited by solubility of the conjugate. Generally, PEGs which are larger than PEGs containing 2300 units are not used. Preferably, a PEG used in the invention terminates on one end with hydroxy or methoxy (methoxy PEG, mPEG) and is on the other end covalently attached to a linker moiety via an ether oxygen bond. The polymer is either linear or branched. Branched PEGs are e.g. described in Veronese, F. M., et al., Journal of Bioactive and Compatible Polymers 12 (1997) 196-207. Useful PEG reagents are e.g. available form Nektar Therapeutics.

Any molecular mass for a PEG can be used as practically desired, e.g., from about 20 kDaltons (Da) to 100 kDa (n is 460 to 2300). The number of repeating units "n" in the PEG is approximated for the molecular mass described in Daltons. For example, if two PEG molecules are attached to a linker, where each PEG molecule has the same molecular mass of 10 kDa (each n is about 230), then the total molecular mass of PEG on the linker is about 20 kDa. The molecular masses of the PEG attached to the linker can also be different, e.g., of two molecules on a linker one PEG molecule can be 5 kDa and one PEG molecule can be 15 kDa. Molecular mass means always average molecular mass.

In the examples below, some preferred reagents for the production of amino-reactive PEGylated IGF-I variants are described. It is understood that modifications, for example, based on the methods described by Veronese, F. M., Biomaterials 22 (2001) 405417, may be made in the procedures as long as the process results in conjugates according to the invention.

The occurrence of up to three potentially reactive primary amino groups in the target protein (up to two lysines and one terminal amino acid) leads to a series of PEGylated IGF-I variants isomers that differ in the point of attachment of the polyethylene glycol) chain.

The invention provides PEGylated forms of IGF-I variant with improved properties. Such PEGylated IGF-I variant conjugates contain one or two PEG groups, which may be linear or branched and randomly attached thereto, whereby the overall molecular weight of all PEG groups in the conjugate is generally about 20 to 80 kDa. Small deviations from this range of molecular weight are possible as long as the PEGylated IGF-I variant does show activity in lowering Abeta peptide levels in the brain. Also PEGylation of IGF-I variants with PEG having molecular weights of more than 80 kDa results in higher bioavailability. However, it is expected that activity may decrease as the molecular weight increases due to reduced IGF-I receptor activation and blood-brain barrier transport. Therefore, the range of 20 to 100 kDa for the molecular weight of PEG has been found by the inventors to be optimal range for a conjugate of PEG and IGF-I variant useful for an efficient treatment of a patient suffering from AD.

As used herein, "molecular weight" means the mean molecular weight of the PEG.

The following PEGylated forms of IGF-I variants are examples of and are contemplated embodiments of the conjugates of the invention:
  monoPEGylated IGF-I variant, wherein the PEG group has a molecular weight of 20 to 80 kDa (460 to 1840 PEG units);
  diPEGylated IGF-I variant, wherein the PEG groups have a molecular weight of about 10-50 kDa (230 to 1150 PEG units) each; and mixtures thereof.

Of particular note is a monoPEGylated IGF-I selected from the group consisting of RRKK, RRKR, RRRK and RKRR, wherein the branched PEG group has a molecular weight of 30-45, preferably 40-45 kDa (about 920 PEG units). For example, based on an average molecular weight of 44 kDa for PEG and a molecular weight of 7.6 kDa for the calculated average molecular weight for such a monoPEG-IGF-I is about 51.6 kDa. Further particular embodiments are a monoPEGylated IGF-I selected from the group consisting of RRKK, RRKR, RRRK and RKRR, where the PEG has an average molecular weight of 30 or 40 kDa.

"PEG or PEG group" according to the invention means a residue containing poly(ethylene glycol) as an essential part. Such a PEG can contain further chemical groups which are necessary for binding reactions; which results from the chemical synthesis of the molecule; or which is a spacer for optimal distance of the parts of the molecule from one another. In addition, such a PEG can consist of one or more PEG side-chains which are linked together. PEG groups with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEGs usually have 2 to 8 arms and are described in, for example, EP-A 0 473 084 and U.S. Pat. No. 5,932,462. Especially preferred are PEGs with two PEG side-chains (PEG2) linked via the primary amino groups of a lysine (Monfardini, C., et al., Bioconjugate Chem. 6 (1995) 62-69).

"Substantially homogeneous" as used herein means that the only PEGylated IGF-I variant molecules produced, contained or used are those having one or two PEG group(s) attached. The preparation may contain small amounts of unreacted (i.e., lacking PEG group) protein. As ascertained by peptide mapping and N-terminal sequencing, one example below provides for the preparation which is at least 90% PEG-IGF-I variant conjugate and at most 5% unreacted protein. Isolation and purification of such homogeneous preparations of PEGylated IGF-I variant can be performed by usual purification methods, preferably size exclusion chromatography.

"MonoPEGylated" as used herein means that IGF-I variant is PEGylated at only one lysine per IGF-I variant molecule, whereby only one PEG group is attached covalently at this site. Such a monoPEGylated IGF-I can be in addition PEGylated at the N-terminus to a certain extent. The pure monoPEGylated IGF-I variant (without N-terminal PEGylation) is at least 80% of the preparation, preferably 90%, and most preferably, monoPEGylated IGF-I variant is 92%, or more, of the preparation, the remainder being e.g. unreacted (non-PEGylated) IGF-I and/or N-terminally PEGylated IGF-I variant. The monoPEGylated IGF-I variant preparations according to the invention are therefore homogeneous enough to display the advantages of a homogeneous preparation, e.g., in a pharmaceutical application. The same applies to the diPEGylated species.

"Activated PEGs or activated PEG reagents" are well-known in the state of the art. Preferably there are used electrophilically activated PEGs such as alkoxybutyric acid succinimidyl esters of poly(ethylene glycol) ("lower alkoxy-PEG-SBA") or alkoxypropionic acid succinimidyl esters of poly(ethylene glycol) ("lower alkoxy-PEG-SPA") or N-hydroxysuccinimide activated PEGs. Any conventional method of reacting an activated ester with an amine to form an amide can be utilized. In the reaction of the activated PEG with IGF-I, the exemplified succinimidyl ester is a leaving group causing the amide formation. The use of succinimidyl esters to produce conjugates with proteins is disclosed in U.S. Pat. No. 5,672,662.

The reaction conditions used have an influence on the relative amount of differently PEGylated IGF-I variants. By manipulating the reaction conditions (e.g., ratio of reagents, pH, temperature, protein concentration, time of reaction etc.), the relative amounts of the different PEGylated species can be varied. In general, the reaction is performed in a buffered aqueous solution pH 8-10, containing 5-15% (v/v) ethanol and 0.5-4% (v/v) ethyleneglycol. The protein:PEG ratio may be 1:0.5 to 1:2 if monoPEGylated variants are desired and 1:2.2 to 1:5 if diPEGylated variants are desired. Reaction temperature and reaction time can be varied according to the knowledge of a skilled artisan, whereby high temperature and long reaction time results in increased PEGylation. If monoPEGylated variants are desired, it is therefore typical to work at 4° C. and for up to 30 minutes. When the PEGylation reagent is combined with IGF-I variant in a reaction buffer which consists of 50 mM sodium borate, 10% ethanol and 1% di(ethylene glycol) (DEG) at a pH of about 9.0, a protein:PEG ratio of about 1:1.5, and a reaction temperature of from 4° C., a mixture of mono-, di-, and trace amounts of the tri-PEGylated species are produced. When the protein:PEG ratio is about 1:3, primarily the di- and oligo-PEGylated species is produced.

IGF-I variant conjugates according to the invention may be prepared by covalently reacting a primary lysine amino group of an IGF-I variant with a bifunctional reagent to form an intermediate with an amide linkage and covalently reacting the intermediate containing amide linkage with an activated poly(ethylene glycol) derivative to form an IGF-I variant conjugate. In the foregoing process, the bifunctional reagent is preferably N-succinimidyl-S-acetylthiopropionate or N-succinimidyl-S-acetylthioacetate, and the activated poly(ethylene glycol) derivative is preferably selected from the group consisting of iodo-acetyl-methoxy-PEG, methoxy-PEG-vinylsulfone, and methoxy-PEG-maleimide.

Especially preferred is the use of a N-Hydroxysuccinimidyl activated branched PEG ester (mPEG2-NHS) of a molecular weight of 40 kDa (Monfardini, C., et al., Bioconjugate Chem. 6 (1995) 62-69; Veronese, F. M., et al, J. Bioactive Compatible Polymers 12 (1997) 197-207; U.S. Pat. No. 5,932,462).

The IGF-I variant conjugates may be prepared by amino-reactive covalent linking of thiol groups to IGF-I variant ("activation") and coupling the resulting activated IGF-I variant with a poly(ethylene glycol) (PEG) derivative. The first step comprises covalent linking of thiol groups via lysine $NH_2$-groups of IGF-I variant. This activation of IGF-I variant is performed with bifunctional reagents which carry a protected thiol group and an additional reactive group, such as active esters (e.g., a succinimidylester), anhydrides, esters of sulphonic acids, halogenides of carboxylic acids and sulphonic acids, respectively. The thiol group is protected by groups known in the art, e.g., acetyl groups. These bifunctional reagents are able to react with the ε-amino groups of the lysine amino acids by forming an amide linkage. The preparation of the bifunctional reagents is known in the art. Precursors of bifunctional NHS esters are described in DE 39 24 705, while the derivatization to the acetylthio compound is described by March, J., Advanced Organic Chemistry (1977) 375-376. The bifunctional reagent SATA is commercially available (Molecular Probes, Eugene, Oreg., USA and Pierce, Rockford, Ill.) and described in Duncan, R. J., Anal. Biochem. 132 (1983) 68-73.

The reaction is carried out, for example, in an aqueous buffer solution, pH 6.5-8.0, e.g., in 10 mM potassium phosphate, 300 mM NaCl; pH 7.3. The bifunctional reagent may be added in DMSO. After completion of the reaction, preferably after 30 minutes, the reaction is stopped by addition of lysine. Excess bifunctional reagent may be separated by methods known in the art, e.g., by dialysis or column filtration. The average number of thiol groups added to IGF-I variant can be determined by photometric methods described in, for example, Grasetti, D. R., and Murray, J. F., in Arch. Biochem. Biophys. 119 (1967) 41-49. The above reaction is followed by covalent coupling of an activated poly(ethylene glycol) (PEG) derivative.

Activated PEG derivatives are known in the art and are described in, for example, Morpurgo, M., et al., J. Bioconjugate Chem. 7 (1996) 363-368 for PEG-vinylsulfone. Linear chain and branched chain PEG species are suitable for the preparation of the compounds of formula I. Examples of reactive PEG reagents are iodo-acetyl-methoxy-PEG and methoxy-PEG-vinylsulfone. The use of these iodo-activated substances is known in the art and is described e.g. by Hermanson, G. T., in Bioconjugate Techniques, Academic Press, San Diego (1996) pp. 147-148.

The further purification of the compounds according to the invention including the separation of mono- and/or diPEGylated IGF-I variants and preferably from N-terminally PEGylated forms may be done by methods known in the art, e.g., column chromatography, preferably ion exchange chromatography especially cationic exchange chromatography.

The percentage of mono-PEG conjugates as well as the ratio of mono- and di-PEG species can be controlled by pooling broader fractions around the elution peak to decrease the percentage of mono-PEG or narrower fractions to increase the percentage of mono-PEG in the composition. About ninety percent mono-PEG conjugates is a good balance of yield and activity. Sometimes compositions in which, for example, at least ninety-five percent or at least ninety-eight percent of the conjugates are mono-PEG species may be desired. In an embodiment of this invention the percentage of mono PEGylated conjugates is from ninety percent to ninety-eight percent.

A "polar amino acid" as used herein refers to an amino acid selected from the group consisting of cysteine (C), aspartic acid (D), glutamic acid (E), histidine (H), asparagine (N), glutamine (Q), arginine (R), serine (S), and threonine (T). Lysine is also a polar amino acid, but excluded, as lysine is replaced according to the invention. Arginine is preferably used as polar amino acid.

Pharmaceutical Formulations

The PEGylated IGF-I according to the invention provides improved stability in the circulation enabling a sustained access to IGF-I receptors throughout the body with low application intervals.

PEGylated IGF-I variants can be administered as a mixture, or as the ion exchange chromatography or size exclusion chromatography separated different PEGylated species. The compounds of the present invention can be formulated according to methods for the preparation of pharmaceutical compositions which methods are known to the person skilled in the art. For the production of such compositions, a PEGylated IGF-I variant according to the invention is combined in a mixture with a pharmaceutically acceptable carrier, preferably by dialysis against an aqueous solution containing the desired ingredients of the pharmaceutical compositions. Such acceptable carriers are described, for example, in Remington's Pharmaceutical Sciences, $18^{th}$ edition, 1990, Mack Publishing Company, edited by Oslo et al. (e.g. pp. 1435-1712). Typical compositions contain an effective amount of the substance according to the invention, for example from about 0.1 to 100 mg/ml, together with a suitable amount of a carrier. The compositions may be administered parenterally. The PEGylated IGF-I according to the invention is administered preferably via intraperitoneal, subcutaneous, intravenous or intranasal application.

The pharmaceutical formulations according to the invention can be prepared according to known methods in the art. Usually, solutions of PEGylated IGF-I variant are dialyzed against the buffer intended to be used in the pharmaceutical composition and the desired final protein concentration is adjusted by concentration or dilution.

Such pharmaceutical compositions may be used for administration for injection or infusion, preferably via intraperitoneal, subcutaneous, intravenous or intranasal application and contain an effective amount of the PEGylated IGF-I variant together with pharmaceutically acceptable diluents, preservatives, solubilizers, emulsifiers, adjuvants and/or carriers. Such compositions include diluents of various buffer contents (e.g. arginine, acetate, phosphate), pH and ionic strength, additives such as detergents and solubilizing agents (e.g. Tween™ 80/polysorbate, Pluronic™ F68), antioxidants (e.g. ascorbic acid, sodium metabisulfite), preservatives (Timersol™, benzyl alcohol) and bulking substances (e.g. saccharose, mannitol), incorporation of the material into particulate preparations of polymeric compounds such as polylactic acid, polyglycolic acid, etc. or into liposomes. Such compositions may influence the physical state stability rate of release and clearance of the monoPEGylated IGF-I according to the invention.

Dosages and Drug Concentrations

Typically, in a standard treatment regimen, patients are treated with dosages in the range between 0.001 to 3 mg, preferably 0.01 to 3 mg of PEGylated IGF-I variant per kg per day over a certain period of time, lasting from one day to about 30 days or even longer. Drug is applied as a single daily subcutaneous or i.v. or i.p. (intraperitoneal) bolus injection or infusion of a pharmaceutical formulation containing 0.1 to 100 mg PEGylated IGF-I per ml. This treatment can be combined with any standard (e.g. chemotherapeutic) treatment, by applying PEGylated IGF-I before, during or after the standard treatment. This results in an improved outcome compared to standard treatment alone.

PEGylated IGF-I according to the invention may be administered only one or two times per week for successful treatment. A further embodiment of the invention is therefore a method for the treatment of Alzheimer's Disease comprising administering to a patient in need thereof a therapeutically effective amount of a PEGylated IGF-I according to the invention with one dosage each in the range between 0.001 to 3 mg, preferably 0.01 to 3 mg of PEGylated IGF-I variant per kg and per 3-8 days, preferably per 7 days. The PEGylated IGF-I used is preferably monoPEGylated IGF-I, preferably as a composition of a lysine-PEGylated IGF-I variant according to the invention and an IGF-I variant which is N-terminally PEGylated wherein the molar ratio is at least 1:1.

The following examples, references and figures are provided to aid the understanding of the present invention, the true scope of which is set forth in the appended claims. It is understood that modifications can be made in the procedures set forth without departing from the spirit of the invention.
Sequence Listing SEQ ID NO: 1 amino acid sequence of human IGF-I (amino acids 1-70 IGF-I; amino acids 71-105 propeptide according to SwissProt P01343).

EXAMPLES

Recombinant human insulin-like growth factor (rhIGF-I) was purchased from PeproTech (Rocky Hill, N.J., USA) via Cell Concepts (Umkirch, Germany) and Des(1-3)-IGF-I was obtained from GroPep (Adelaide, Australia). The polyethylene glycol (PEG) reagent was delivered from Nektar Ltd. (San Carlos, Calif., USA). All other chemicals and solvents for this investigation were of the highest purity available. IGF-I variants can be produced recombinantly according to the state of the art by e.g. using site directed mutagenesis in combination with expression methods preferably in E. coli as e.g. described in U.S. Pat. No. 6,509,443 or U.S. Pat. No. 6,403,764.
PEGylation of IGF-I IGF-I isomers with PEGylation at a single site (monoPEG-IGF-I) were produced. MonoPEG-IGF-I was prepared by the conjugation of lysine ε-amino groups at the surface or on the N-terminus of the IGF-I molecule with an activated branched PEG moiety of 40 kDa molecular weight. PEGylation reaction mixture contained rhIGF-I and 40 kDa PEG-NHS reagent at 1:1.5 molar ratio in 50 mM sodium borate buffer (10% etanol and 1% DEG), pH 9.0. The reaction was performed for 30 min at 4° C. Based on the average molecular weight of 44 kDa for the used PEG moiety and a molecular weight of 7.6 kDa for IGF-I, the calculated average molecular weight for monoPEG-IGF-I was expected around 51.6 kDa.
Separation of Positional PEG-IGF-I Isomers by Ion Exchange Chromatography A purification scheme with a preparative strong-cation exchange column (TOSOH-BIOSEP, SP-5PW, 30 mm i.d. and 75 mm length) was used to prepare pure monoPEG-IGF-I isoforms. The buffer system consisted of 7.5 mM sodium acetate, 10% ethanol and 1% diethylene glycol, adjusted to pH 4.5 (buffer A) and 20 mM potassium phosphate, 10% ethanol and 1% diethylene glycol, adjusted to pH 6.5 (buffer B).

The column was pre-equilibrated with 25% buffer B. After loading the PEG-IGF-I samples, the column was washed with 35% buffer B, followed by an ascending linear gradient to 65% buffer B to separate the isomers. For the elution of the non-PEGylated IGF-I the system was switched to modified buffer B with a pH. 8.0. The flow rate was 8 ml/min and the detection was performed at 218 nm. The resulting protein samples were collected manually and stored aliqouted at −20° C. to be analyzed by a variety of protein chemical and biological assays (see below).

An analytical strong-cation exchange column (TOSOH-BIOSEP, SP-NPR, 2.5 μm particle size, 4.6 mm diameter, 3.5 cm length) was used to investigate the purity of the separated positional isomers. For this analytical column we used the same mobile phases as for the preparative one but with reduced flow rate and running time. The protein concentration of the monoPEG-IGF-I isomers was determined by spectrophotometry, based on the 280 nm absorption ($E_{280}^{1mg/ml}$=0.584) of the protein moiety of monoPEG-IGF-I.
Analysis of monoPEG-IGF-I Purity Individual monoPEG-IGF-I isomers were analyzed by 4-12% Tris-glycine SDS-PAGE under non-reduced or reduced conditions. The proteins were fixed and stained using the Simple Blue SaveStain (Invitrogen, Basel, Switzerland).
Mass Spectroscopy Identification of monoPEG-IGF-I Isomers The purified monoPEG-IGF isomers were cleaved with Asp-N to identify the four possible PEGylation sites at the N-terminus, at K27, K65 or K68. The cleavage buffer consisted of 100 mM Tris/HCl pH 8.0 with 0.04 μg/μl Asp-N(Roche Diagnostics GmbH, DE). 20 μg monoPEG-IGF were incubated in cleavage buffer for 16 h at 37° C. with 1 μg Asp-N. After 16 h the reaction mixture was reduced by addition of TCEP (10 mM) for 1.5 h at 37° C. Subsequently the reaction solution was quenched by addition of ¹⁄₂₀ volume of 10% TFA to finalize the cleavage reaction. The obtained peptide mixtures were either directly analyzed by online-HPLC ESI mass spectrometry, HPLC or stored at −80° C.

For ESI-LC-MS analysis, the peptide mixtures were separated on an Agilent 1100 HPLC system equipped with a Phenomenex Jupiter C18 reversed phase column (1×250 mm, 5 μm, 300 Å) with a flow rate of 40 μl/min. The UV signal was also recorded at 220 nm. A Q-ToF II or LCT mass spectrometer (Micromass) was directly coupled to the HPLC system. ESI-ToF spectra were recorded with 1 scan/s in the mass range from 200-2000 m/z. UV and TIC spectra were evaluated and each peptide could be assigned to a single peak in the chromatogram.

For HPLC analysis, peptide mixtures were separated on an Agilent 1100 HPLC system equipped with a Phenomenex Jupiter C18 reversed phase column (1×250 mm, 5 µm, 300 Å) with a flow rate of 40 µl/min. The UV signal was also recorded at 220 nm. PEG peptides were shifted in retention time towards higher acetonitrile concentrations and were manually collected and submitted to N-terminal Edman degradation.

Conditions for HPLC runs (Solvent A: 0.1% TFA in water, solvent B: 0.1% TFA in Acetonitrile) are shown in table 1:

TABLE 1

Gradient:

| Time | % B |
|---|---|
| 0 | 0 |
| 10 | 0 |
| 30 | 20 |
| 60 | 28 |
| 70 | 48 |
| 80 | 100 |
| 85 | 100 |
| 86 | 0 |
| 96 | 0 |

N-terminal Edman degradation sequencing was conducted on an Applied Biosystems Procise system according to N-terminal Edman degradation sequencing was conducted on an Applied Biosystems Proteinsequencer Procise 492 with the procise system control software according to the manufacturers instructions. 20 µl of fractions collected from HPLC runs were directly applied to BioBrene Plus™ conditioned micro TFA filters, Filters were dried under argon covered with cartridge seals and introduced into the proteinsequencer. Automatic standard programs were used to conduct the sequential degradation of the polypeptide. Analysis of the HPLC chromatograms from each degradation cycle with Applied Biosystems data evaluation software 610A revealed the positions each amino acid. Cysteins as well as modified amino acids like pegylated lysine appeared as a gap in the chromatogram.

Oligonucleotide Array Transcriptional Analysis

For in vitro transcriptional profiling of different monoPEG-IGF-I isomers, IGF-IR stably transfected NIH-3T3 cells were serum-starved for 2 h and incubated in the absence of serum over 24 h with 0.1 or 1 µg/ml rhIGF and 1 µg/ml of the respective monoPEG-IGF-I isomers or the mixture of all isomers obtained without separation. Subsequently, the cultured cells were harvested and the total cellular RNA was extracted with RNA-Bee™. From each sample 10 µg RNA were reversely transcribed, labelled and processed by using commercial kits according to the supplier's instructions (Invitrogen, Basel, Switzerland; Ambion, Huntingdon, UK). The methods for alkaline heat fragmentation and the hybridization conditions for MOE 430A GeneChip arrays were standard procedures provided by the manufacturer (Affymetrix, US). Fluorescence (cell intensities) of the arrays was recorded with a confocal laser scanner and data were analyzed using MAS 5.0 software (Affymetrix, US). The expression level for each gene was calculated as normalized average difference of fluorescence intensity as compared to hybridization to mismatched oligonucleotides, expressed as average difference (AD). Each experiment was performed in triplicate in order to account for biological variation.

The following two criteria were chosen for the selection of differentially expressed genes: i) the mRNA levels value of the treated cells had to be at least five fold higher or five fold lower as compared to the untreated cells. ii) The standard deviation must be significantly smaller than the absolute change in average difference and the calculated confidence level of a gene was set greater than 97% ($p<0.03$).

IGF-IR Phosphorylation Assay

NIH-3T3 cells stably transfected with human IGF-IR were used for these experiments between passages 2 and 4. Cells were cultivated either in uncoated 24- or in 96-well plates and grown until 70% confluency. Subsequently, cells were serum-starved over night and then incubated with rhIGF-I or the respective PEG-IGF-I peaks (or peak mix) for 30 minutes. Cells were then either lysed in Laemmli buffer for Western or fixed with 4% paraformaldehyde for 30 minutes for in-cell analysis of IGF-IR phosphorylation. For Western analysis, protein extracts were separated by 10% Bis-Tris SDS-PAGE and blotted onto nitrocellulose membranes. Blots were co-incubated with mouse-anti-phospho-tyrosine (4G10, 1:1000; Upstate) and rabbit-anti-IGF-IR (C-20, 1:1000; Santa Cruz) primary antibodies and labeled with anti-mouse-Alexa680 (1:10000; Molecular Probes) and anti-rabbit-IRDye800 secondary antibodies (1:10000; Jackson). For in-cell analysis, fixed cells were blocked and permeabilized with 2% goat serum and Triton X-100 (0.1%) and incubated with the same primary and secondary antibodies. Fluorescence detection of protein bands was performed with the Odyssey imaging system (Licor Biosciences). From digital images, pixel intensity of protein bands was quantified and dose response curves were analyzed using GraphPad Prism software. Phosphotyrosine levels were normalized with IGF-IR values obtained from the same regions of interest to obtain real IGF-IR activation changes. Experiments were performed in duplicate and repeated 3 times to obtain 6 independent investigations per dose. Data were expressed as means±SEM.

In Vivo Experiments with rhIGF-I and PEG-IGF-I Isomers

A mouse model for Alzheimer's disease consisting of single-transgenic AAP and double-transgenic PS2AAP mice (Richards, J. G., et al., J. Neurosci. 23 (2003) 8989-9003) was used to investigate the effect of rhIGF-I (and monoPEG-IGF-I) on brain amyloidosis that has been recently shown in other mouse and rat models (Carro, E., et al., Nat. Med. 8 (2002) 13904397). The PS2APP mouse model has been shown to develop an amyloidosis with measurable Abeta levels at 2 months and onset of plaque deposition at 8 months of age (Richards, L G., et al., J. Neurosci. 23 (2003) 8989-9003). Single-transgenic APP mice show very similar Abeta levels at this young age and therefore were included into the groups. We analyzed a pre-plaque age (2-3 months) to investigate the effects of rhIGF-I and PEG-IGF-I isomers on soluble brain Abeta levels. All experiments were performed in accordance with Swiss animal protection rights and suffering of the animals was kept to a minimum. From stock solutions in 1 mM HCl (rhIGF-I) or PBS with 10% glycerol (monoPEG-IGF-I isomers) injection solutions were prepared in 0.9% NaCl with solvent less than 1%. Controls were injected with 0.9% NaCl. Injections were performed i.p. under slight isoflurane anesthesia. At different times points after injection (2 h, 6 h, 24 h, 48 h or 72 h) animals were sacrificed under isoflurane anesthesia. Mice were decapitated and brains were removed for isolation of the telencephalon (cortex including hippocampus). Cortical protein extracts were prepared in hypotonic lysis buffer containing 4 mM Tris pH 7.4 and 320 mM Sucrose (both Fluka) with protease and phosphatase inhibitor cocktails (both Sigma). Sample buffer was Laemmli containing 8 M urea (Fluka). Proteins were separated by 4-12% Bis-Tris SDS-PAGE and blotted onto nitrocellulose membranes. Blots were co-incubated with mouse-anti-amyloid precursor protein (APP) (WO-2 clone, 1:5000; The Genetics Company) detecting APP, the C99 fragment and Aβ and goat-anti-Actin (C-11, 1:5000; Santa Cruz) primary antibodies and labeled with anti-mouse-Alexa680 (1:10000; Molecular Probes) and anti-goat-IRDye800 secondary antibodies (1:10000; Jackson). Fluorescent detection of protein bands was performed with the Odyssey imaging system (Liam Biosciences). From digital images, pixel intensity of protein bands was analyzed using GraphPad Prism software. Data were expressed as means±SEM.

All values were normalized for actin (or albumin as control protein) and the specific ratios (C99/APP, Aβ/APP, C99/Aβ) were calculated. The C99/APP ratio gives information about the activity state of β- and γ-secretase because C99 is the product of and the substrate of β-secretase; alterations in this measure would indicate a modulatory effect on one of these secretases independent on the later fate of AO. With constant C99/APP levels after a particular treatment, the C99/Aβ ratio monitors the clearance of Aβ independent on its production, being higher with increased and lower with decreased clearance rate. Furthermore, Aβ was normalized for APP because its production depends on transgenic APP expression which varied between individual mice. The ratio calculations were performed for every individual animal. All obtained data are expressed in % of an untreated control group included in every experiment. Individual experiments with 2-5 animals per dose/time interval were repeated 2-4 times. Statistical differences were assessed from means±SEM by unpaired t tests with p<0.05 considered statistically significant.

Example 1

Chromatographical Separation of monoPEG-IGF-I Positional Isomers

IGF-I contains 4 amino groups as potential PEGylation sites and 4 possible monoPEGylated IGF-I (monoPEG-IGF-I) isomers were expected. Further derivates were expected to be oligoPEGylated depending on the reaction conditions. A strong-cation high pressure liquid chromatography method (IEC-HPLC) was developed for the separation of PEG-IGF-I or -Des(1-3)-IGF-I isomers based on their local charge differences. A preparative elution profile of 5 mg PEG-IGF-I is shown in FIG. 1. The result of this method was a separation into 5 major peaks, 3 peaks with baseline separation and 2 with partial separation. The decrease of the baseline absorption towards the end of the chromatogram suggests no additional monoPEGylated IGF-I species eluting at higher retention time. An additional peak appears between peak 3 and 4 resulting from the switch to the modified buffer B with different pH. Analytical IEC-HPLC was used to estimate the purity of the individual isomers and contamination by other positional isomers in the IEC fractions. All monoPEGylated peaks had a purity of >99%.

Example 2

SDS-PAGE Analysis of monoPEG-IGF-I Isomers

Figure 2:
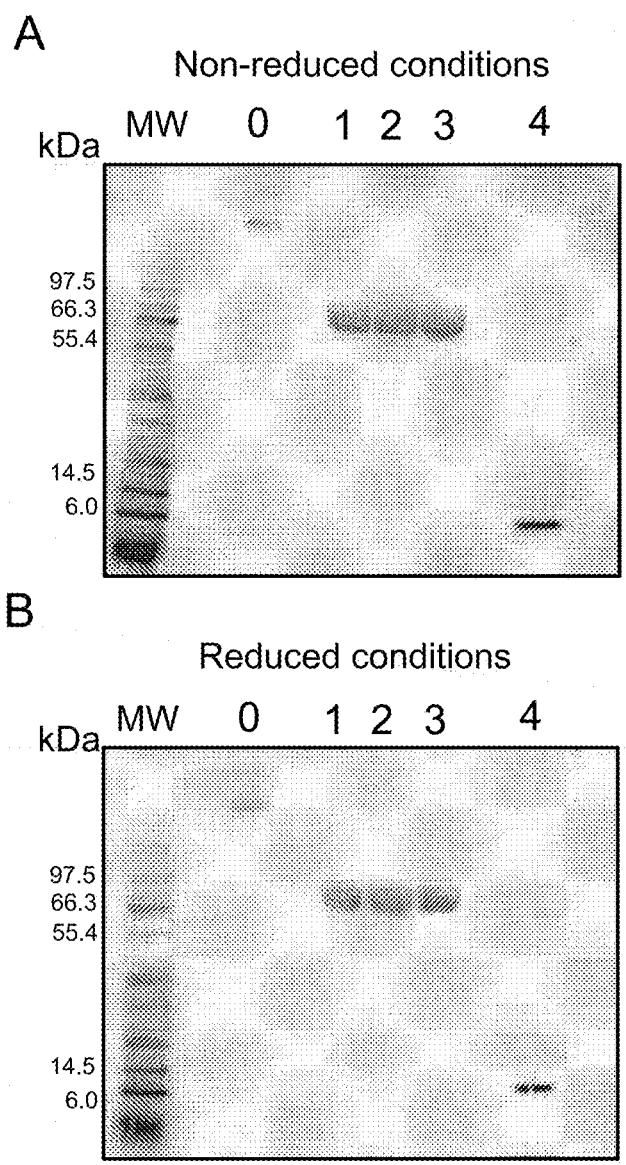
FIG. 2: SDS-PAGE analysis of monoPEG-IGF-I peaks. The five purified peak fractions (numbered 0-4) were electrophoresed by 4-12% Tris-glycine SDS-PAGE under non-reduced (A) and reduced (B) conditions and gels were stained for protein with Coomassie blue. MW, molecular weight marker.

SDS-PAGE was performed both under non-reducing and reducing conditions to evaluate potential unwanted cross-linking of different IGF-I molecules through intermolecular disulfide bridges. Both conditions yielded similar results indicating that no significant amount of the protein was abnormally cross-linked (FIG. 2). The SDS-PAGE analysis showed that peak 0 had an apparent molecular weight of >100 kDa whereas the major detected bands were peaks 1-3 at ~70 kDa; additionally, peak 4 was detected at ~7 kDa, a size expected for unPEGylated IGF-I (FIG. 2). From this running profile and the retention times obtained in the HPLC we concluded that peak 0 consists most probably of di- and oligoPEG-IGF-I. In contrast, peaks 1-3 were designated as 3 different monoPEG-IGF-I isomers. There was a discrepancy between the expected molecular weight for monoPEG-IGF-I (51.6 kDa) and the apparent size of ~70 kDa; however, the observed higher apparent molecular weight can be explained by the larger hydrodynamic volume of PEG due to water binding considerably slowing the electrophoretic motility of PEG-IGF-I and increasing the apparent molecular weight (Foser, S., et al., Pharmacogenomic J. 3 (2003) 319).

Taken together, IEC-HPLC and SDS-PAGE experiments indicate that the purity of the IEC fractions can be considered sufficiently pure for further characterization.

PEGylation and separation of monoPEG-Des(1-3)-IGF-I was performed correspondingly to rhIGF-I and yielded similarly 3 major monoPEG-Des(1-3)-IGF-I peaks.

Example 3

Analysis of monoPEG-IGF-I Isomers

Figure 3:
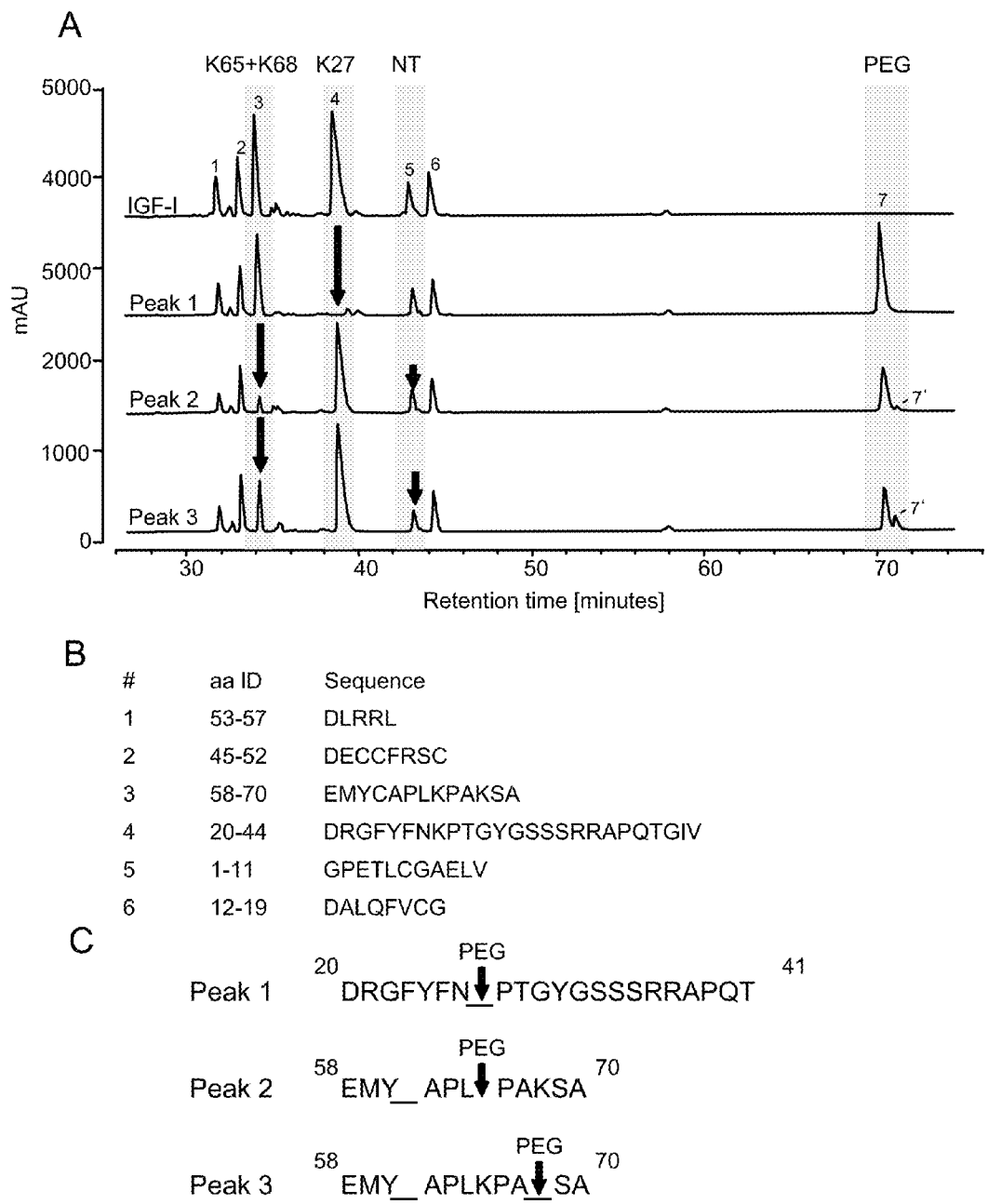
FIG. 3: Peptide analysis of monoPEGylated IGF-I peaks 1, 2 and 3. The purified monoPEGylated peaks 1, 2 and 3 were digested with Asp-N and the peptide fragments separated by HPLC. Peptide sequences of the PEGylated fragments were obtained by Edman N-terminal peptide degradation as described. A., HPLC analysis yielded 6 different peptide fragments for rhIGF-I at retention times between 30 and 45 minutes and a major fragment 7 (and a minor fragment 7') for the PEGylated peaks at ~70 minutes retention time. Arrows indicate the major relative changes in peptide fragments in the different peaks as compared to rhIGF-I. B., Peptide sequence of the 6 fragments (SEQ ID NOS: 2-7, respectively in order of appearance) obtained from Asp-N cleavage of rhIGF-I. The lysines (K) are marked in bold and occur in fragments 3 and 4. Fragment 5 illustrates the N-terminal peptide. C., Peptide sequence of the PEGylated peptide fragments 7 after Edman degradation (SEQ ID NOS: 8-11, respectively in order of appearance). Cystein and PEGylated lysine residues deliver breaks in the peptide sequence.

Cleavage of rhIGF-I with Asp-N delivered 6 independent peptide fragments that were separated by HPLC between 30 and 45 minutes retention time (FIG. 3A, upper panel). After cleavage of the purified peaks 1 to 3 (FIG. 3A, lower panels), different distributions of the 6 fragments and the occurrence of an additional fragment (fragment 7) was observed eluting at ~70 minutes retention time. For peak 1, specifically peptide fragment 4 was diminished with a concomitant increase of fragment 7. For peak 2, we observed a clear decrease in fragment 3 and a slight decrease in fragment 5 and the appearance of a major and a minor PEG fragment (7 and 7'). Similarly, HPLC analysis of peak 3 yielded a clear decrease in fragments 3 and 5 with the concomitant occurrence of fragments 7 and 7'. FIG. 11B shows the peptide sequences of the respective fragments as obtained by Asp-N cleavage of rhIGF-I. Using Edman N-terminal peptide degradation we analyzed the peptide sequences of the major fragments 7 obtained with the PEGylated peaks 1, 2 and 3. Thereby, cysteins and PEGylated amino acids delivered breaks in the peptide sequence. Using this analysis peak 1 could be clearly mapped as rhIGF-I being PEGylated at K27 (FIG. 3C). For peak 2, the major fragment 7 (>90%) was mapped as K65 being PEGylated since K68 was confirmed as unmodified lysine (K) by Edman degradation. In contrast, the fraction of peak 0.3 delivered a PEGylation at K68 (gap in the sequence) with K65 resulting in a signal in the Edman degradation HPLC chromatogram (FIG. 3C). The minor peak 7' could not be sequenced by Edman degradation indicating that the N-terminus was not accessible to the reaction, most probably by PEGylation. Taken together, these data indicate that peak 1 consists of the K27 PEGylated isomer, peak 2 is IGF-I PEGylated at K65 and peak 3 is K68 PEGylated with a significant amount of N-terminally PEGylated IGF-I.

Example 4

Transcriptional Profiling of rhIGF-I and the monoPEG-IGF-I Isomers

Figure 4:
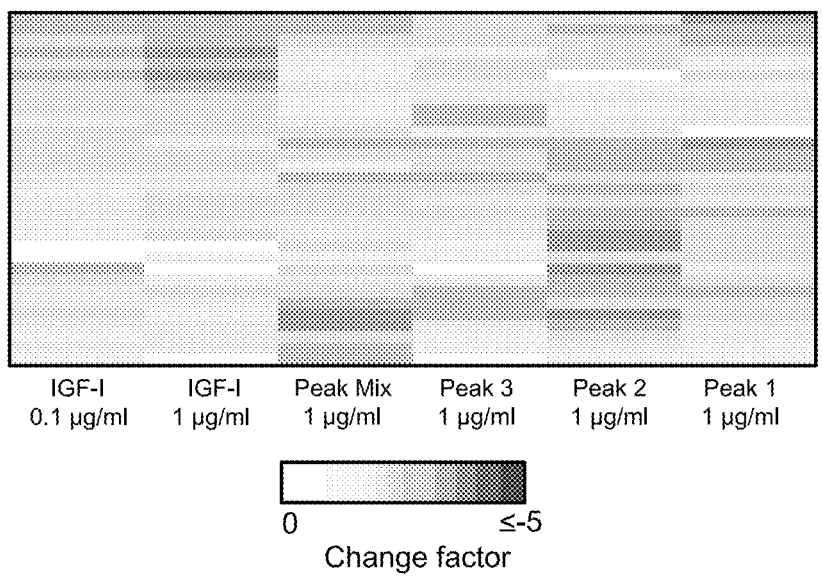
FIG. 4: Hierarchical clustering of AD of the different global expression profile from IGF-I and the monopegylated isomers. The incubation time of the IGF-I and the pegylated variants was 24 h; using the mouse cell line NIH-3T3. The conditions for the data analysis are described in the text (A) Clusters of downregulated genes. (B) Clusters of upregulated genes.
Figure 4:
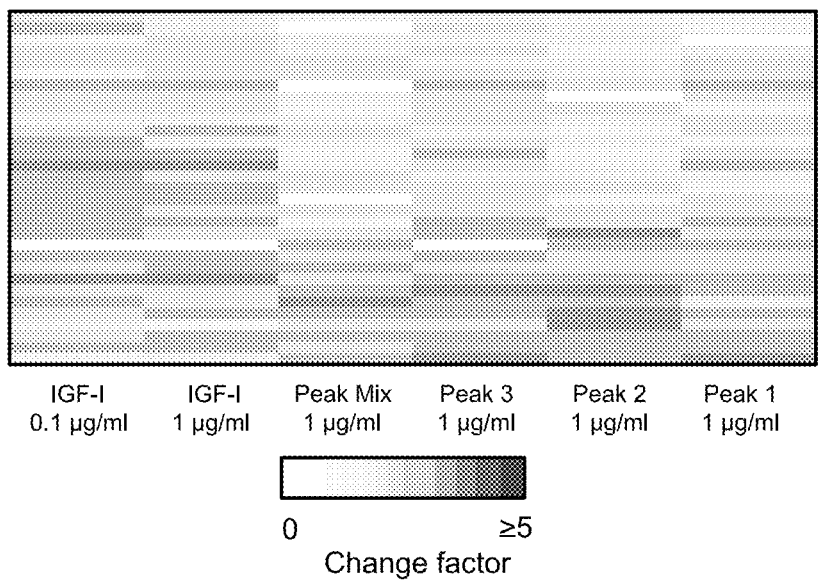

Using DNA micorarrays we determined the transcriptional response of NIH-3T3 cells stably transfected with human IGF-IR over a 24 h treatment with rhIGF-I or the PEG-IGF-isomers. Therefore, we stimulated the cells with 0.1 and 1 µg/ml of IGF-I or with 1 µg/ml of monoPEG-IGF-I peaks or the peak mixture obtained from the PEGylation reaction. We compared the global transcriptional activity of stimulated cells with control cultures using a commercial chip type (MOE 430A; Affymetrix Inc.) containing probe-sets for about 14,000 mouse genes including all known IGF-I response genes. The mRNA abundance was expressed as average difference (AD) between perfect match oligonucleotide probes and a corresponding probe with mismatch in the center position. We considered only genes with a change factor of greater than five and 97% reproducibility (p-value<0.03) within three biological replicates. This analysis yielded to a total of 162 genes, 86 upregulated and 76 downregulated by all IGF-I variants. A general correlation profile for transcriptional activity of different monoPEG-IGF-I isomers is illustrated in form of a hierarchical cluster of the up- and downregulated genes in FIG. 4. An inspection of the induction levels of individual gene of 0.1 µg/ml and 1.0 µg/ml IGF-I shows that the selected clusters are very similar. Peak 3 generates a similar expression profile as unpegylated IGF-I at the same concentration and it is more potent than the PEG-IGF mixture and the other peaks. Interestingly, peak 2 triggers a similar transcriptional response like the PEG-IGF mixture. Consistent with the biological activity Peak 1 shows the weakest transcriptional response, indicating that pegylation interferes with receptor interaction.

Examples 5 and 6

In Vitro IGF-IR Phosphorylation by rhIGF-I and monoPEG-IGF-I

Figure 5:
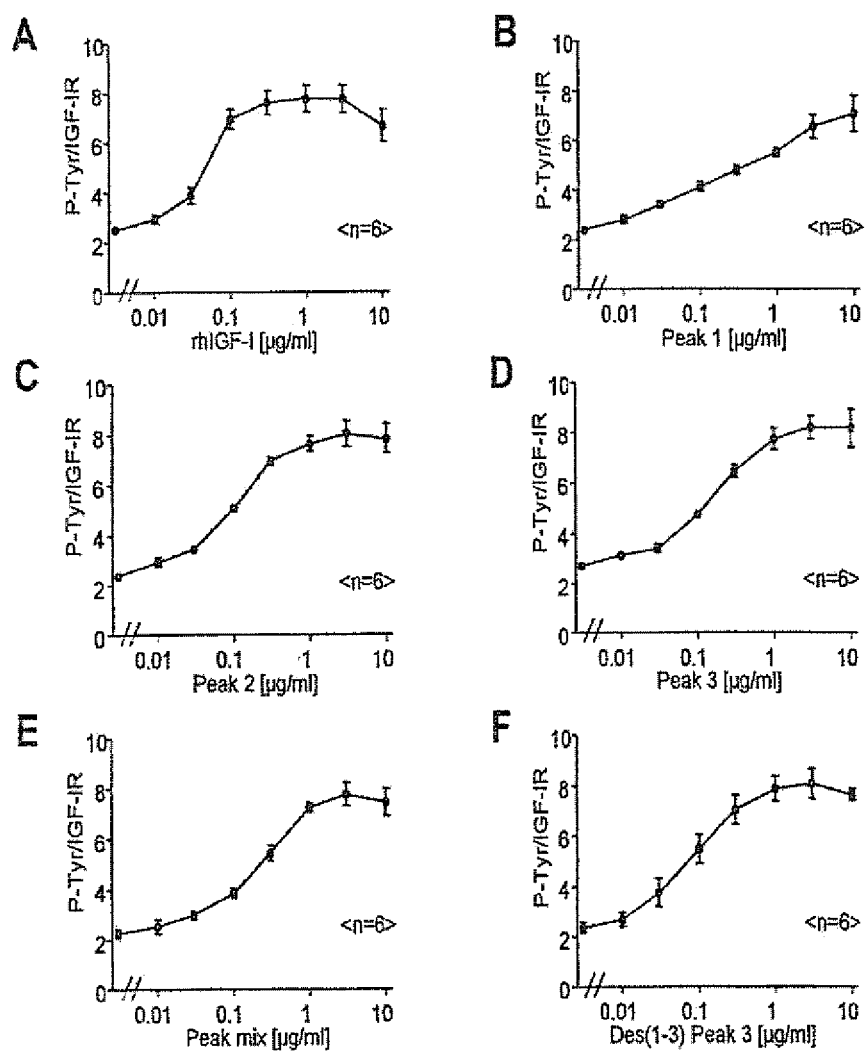
FIG. 5: IGF-IR phosphorylation by rhIGF-I and monoPEG-IGF-I. NIH-3T3 cells stably transfected with human IGF-IR were serum-starved over night and incubated with increasing doses (0.01-10 µg/ml) of rhIGF-I or monoPEG-IGF-I isomers (peak 1, 2, 3, peak mix, Des(1-3) peak 3) for 30 minutes. Subsequently, cells were processed for Western or in-cell analysis as described in Methods. Dose response curves with rhIGF-I (A), peak 1 (B), peak 2 (C), peak 3 (D), peak mix (E) and Des(1-3) peak 3 (F), respectively. The phosphorylation signal was normalized for IGF-IR levels in the individual wells. Data points show means±SEM of 6 measurements from 3 independent cultures.
Figure 7:
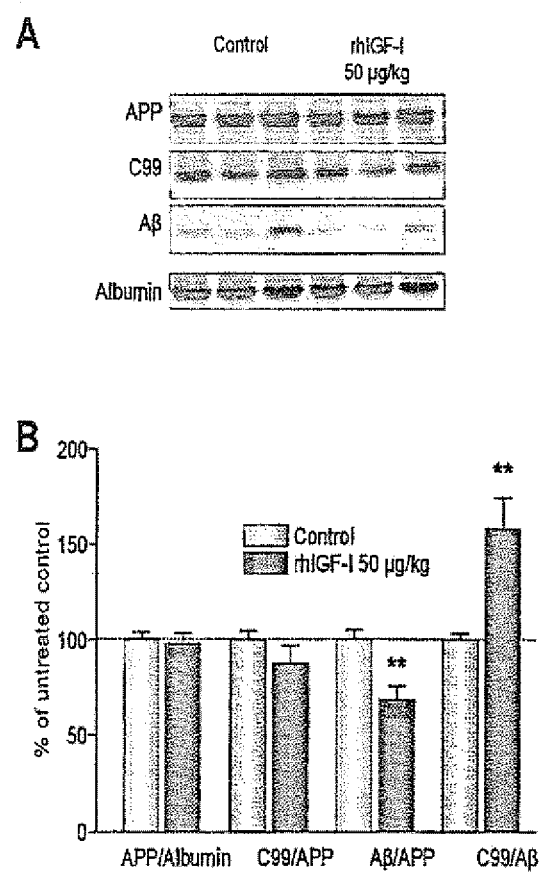
FIG. 7: In vivo brain abeta lowering of rhIGF-I in PS2APP mice. Double-transgenic PS2AAP mice at 2-3 months (n=10) were treated for 2 h with rhIGF-I (50 μg/kg i.p.). Cortical extracts were prepared and APP, C99, Abeta and control protein (albumin) levels evaluated as described in Methods. From albumin-normalized values, the ratios C99/APP, Abeta/APP and C99/Abeta were calculated and are expressed as % of untreated controls and represent means±SEM. A, representative Western Blots of 2 months old cortical extracts. Note the clear reduction in Abeta levels while other levels were unchanged by rhIGF-I treatment. B, quantitative analysis of cortical extracts from PS2APP mice (**, $p<0.01$ vs. untreated control).

For the in vitro analysis of IGF-IR activation, NIH-3T3 cells stably expressing the human IGF-IR were used. After serum starvation over night, cells were treated with increasing doses of rhIGF-I or the respective PEG-IGF-I isomer (0.003-10 µg/ml). Western analysis of phosphorylated IGF-IR was performed according to described above and the obtained dose response curves were fitted with a one-site binding kinetics including the Hill coefficient ($n_H$); quantitative data of the association curves are shown in the table in FIG. 6. The dose response of rhIGF-I (FIG. 5A) yielded an $EC_{50}$ of 6.3 nM and nearly occurred in an all-or-nothing fashion with an $n_H$ of 2.27 (FIG. 6). In contrast, peak 1 of monoPEG-IGF-I did not show a clear dose response with no saturation, an $n_H$ of 0.34 and an estimated $EC_{50}$ of 91.5 nM (FIGS. 5B, 6). The peaks 2 and 3 (FIGS. 5C and 5D) showed similar binding affinities with $EC_{50}$ values of 13.4 and 21.5 nM, respectively (FIG. 6). In both cases, pH was regular with 1.27 and 1.19, respectively. The peak mixture demonstrated a similar IGF-IR activation pattern with slightly lower affinity with an $EC_{50}$ of 28.8 nM and regular $n_H$ of 1.28 (FIGS. 5E, 7). Finally, PEG-Des(1-3)-IGF-I peak 3 had the highest affinity of all PEG isomers with an $EC_{50}$ of 10.8 nM and regular $n_H$ of 1.08 (FIGS. 5F, 7). The data indicate that all peaks with exception of peak 1 specifically activated the human IGF-IR with a 2-5 fold loss of affinity as compared to rhIGF-I.

Example 7

In Vivo Abeta Lowering in 2 Months Old PS2APP Mice by rhIGF-I

Double-transgenic PS2APP mice were used to analyze the short-term effects of rhIGF-on brain Abeta load. We treated these mice with 50 µg/kg rhIGF-I i.p. and analyzed cortical Aβ 2 h after injection. FIG. 7A shows Western Blots of brain extracts from 2 months old mice. Whereas APP, C99 and control protein (albumin) levels appear unchanged by rhIGF-I, Abeta levels were reduced 2 h after rhIGF-I injection. Quantitative analysis was performed and ratios of the respective pixel intensities were calculated to obtain information about potential effects of rhIGF-I on Abeta production. This analysis revealed that the APP/control protein (97.5±5.7% of control) and C99/APP (87.2±9.8% of control) ratios were not changed indicating that neither transgenic APP expression nor APP processing was altered 2 h after treatment with rhIGF-I (FIG. 7B). In contrast, Abeta/APP significantly dropped to 68.4±7.1% of control (p<0.01) and C99/Abeta increased to 157.9±16.6% of control (p<0.01) indicating that rhIGF-I lowered Abeta. Taken together, these data suggest that treatment of young PS2APP mice for 2 h with rhIGF-I mainly increases Abeta clearance from the brain.

Example 8

Time Course of In Vivo Abeta Lowering in PS2APP Mice by rhIGF-I

Figure 8:
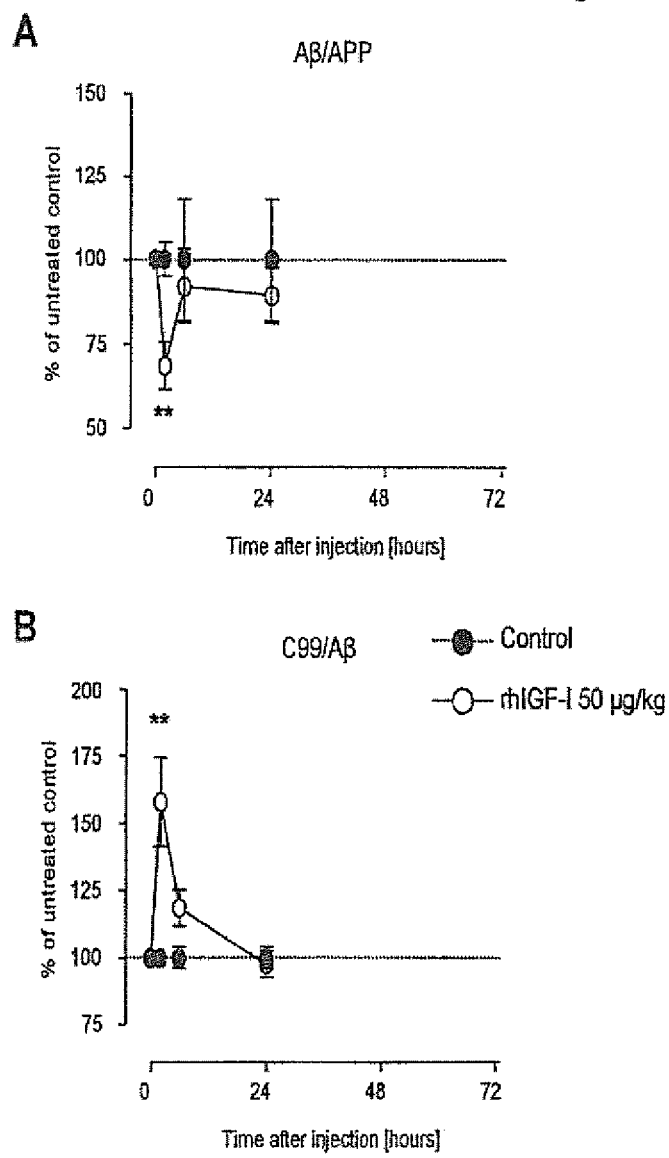
FIG. 8: Time course of in vivo Abeta lowering in PS2APP mice by rhIGF-I. Two months old mice were treated for 2, 6 or 24 h with rhIGF-I (50 μg/kg i.p.). Subsequently, Abeta/APP and C99/Abeta levels were evaluated and ratios calculated as described. Data are expressed as % of untreated controls and represent means±SEM (n=10-13). A, Abeta/PP and B, C99/Abeta ratios at 2, 6 and 24 h after injection (**, $p<0.01$ vs. untreated control).

For evaluation of the time course of this short-term effect of rhIGF-I on soluble brain Abeta, young PS2APP mice devoid of brain plaques (2 months old) were treated by i.p. injection of 50 µg/kg rhIGF-I and cortical APP, C99, Abeta and actin levels were detected 2, 6 or 24 h later. APP/albumin and C99/APP ratios were not significantly changed by rhIGF-I at any time point investigated. Lowering of Abeta/APP by rhIGF-I was observed at 2 h after injection whereas the effect was absent after 6 and 24 h (FIG. 8A). Similarly, the increase in Abeta reduction monitored by the C99/Abeta ratio was only detectable at 2 h and disappeared at 6 and 24 h (FIG. 8B). This indicates that the effect of rhIGF-I on Abeta clearance was of short duration probably due to the short half-life of isolated IGF-I in the blood stream.

Example 9

Figure 9:
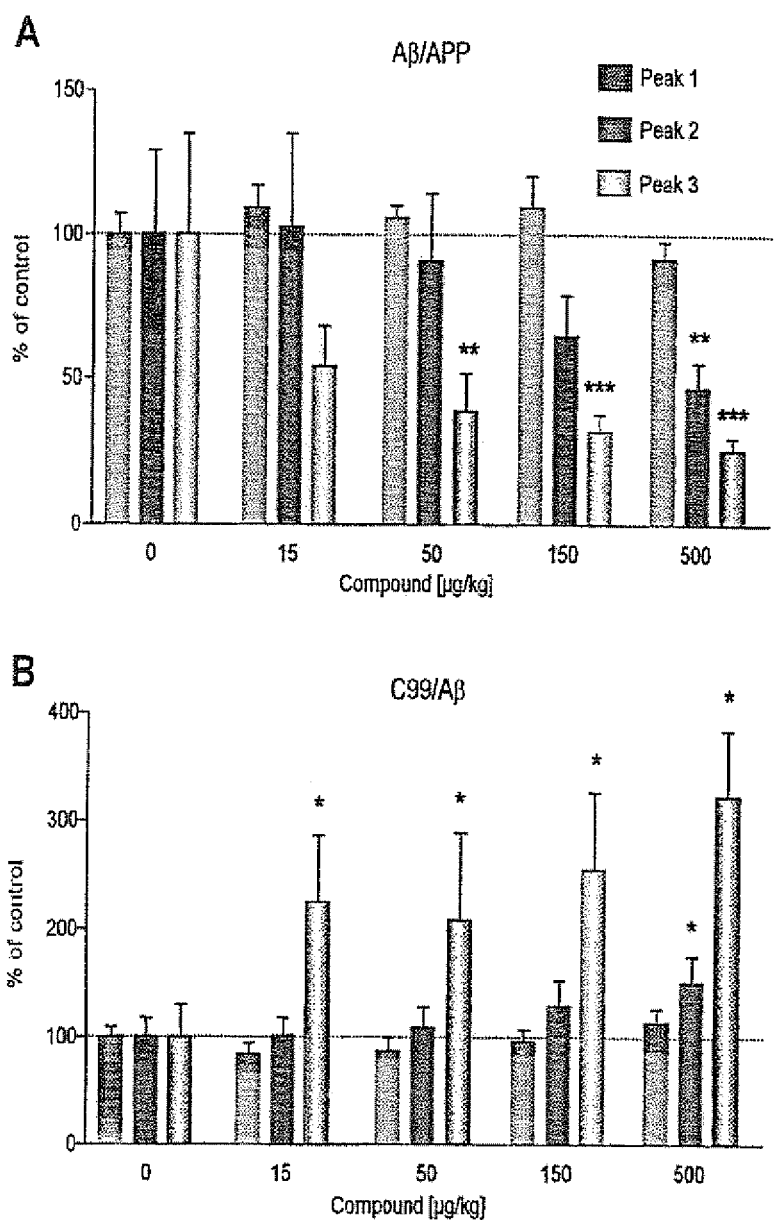
FIG. 9: In vivo abeta lowering in AAP and PS2APP mice by peaks 1-3. Experiments were performed in mixed populations of single-transgenic APP and double-transgenic PS2APP mice. Abeta/APP and C99/Abeta ratios for peak 1, 2 and 3 are shown together for direct comparison of their relative effects on Abeta lowering and clearance (n=8-10). A, Abeta/APP ratios showing the effects of peaks 1-3 on brain Abeta load. B, C991 Abeta ratios of peaks 1-3 demonstrating the clearance of Abeta from the brain (*, $p<0.05$; , $p<0.01$; *, $p<0.001$ vs. untreated control).

Comparative Analysis of Peaks 1-3 for In Vivo Abeta Clearance Potency in 2 Months Old APP and PS2APP Mice In this example, data for PEG-IGF-I peaks 1-3 are shown together for direct comparison of the potencies for Abeta lowering and Abeta clearance. Similarly to rhIGF-I, APP/Actin (actin was used here as control protein) or C99/APP ratios were not altered by any concentration of peak 1, 2 or 3. Peak 3 had the highest potency in reducing Abeta/APP at 6 h after i.p. injection (FIG. 9A). In contrast, peak 1 was without activity over the whole concentration range tested and peak 2 only exerts a significant effect on lowering Abeta/APP at the highest concentration used (500 µg/kg). Similarly, as shown in FIG. 9B, peak 3 was the only compound active at low doses (15-50 µg/kg) in increasing the C99/Abeta ratio representative for an increased Abeta clearance. Also in this evaluation, peak 1 was inactive and peak 2 only exerted significant effects at 500 µg/kg. Taken together, these data suggest that peak 3 is the most active monoPEG-IGF-I isomer in this in vivo experimental paradigm.

Example 10

Time Course of In Vivo Abeta Lowering in PS2APP Mice by Peak 3

Figure 10:
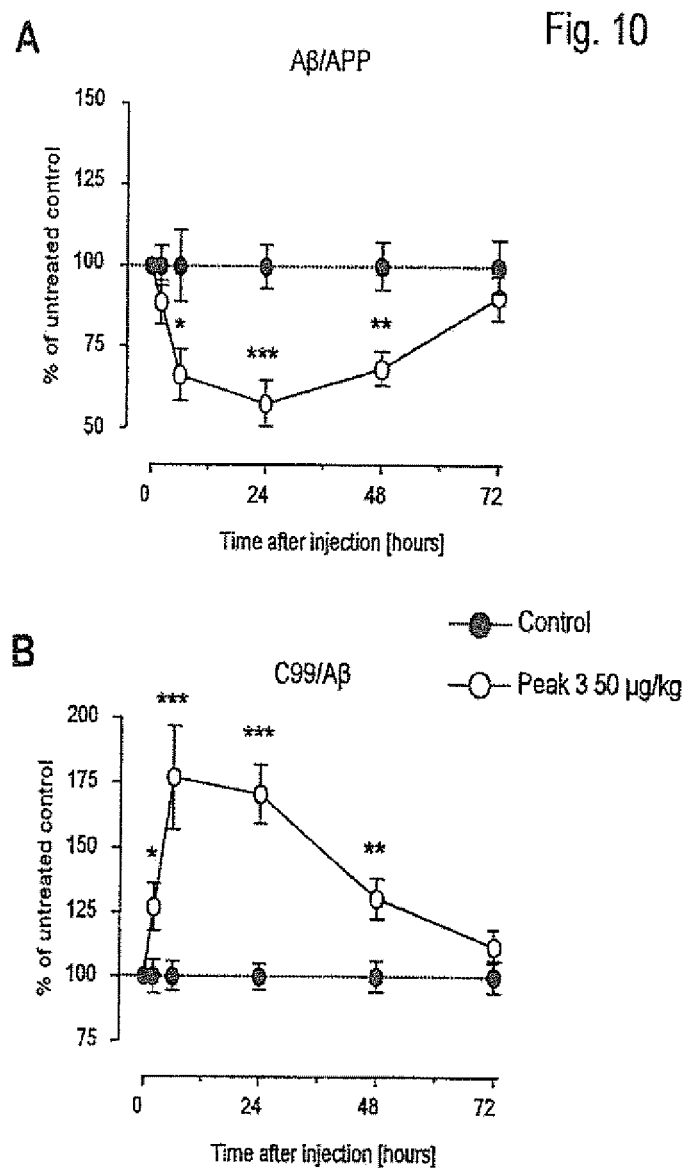
FIG. 10: Time course of in vivo Abeta lowering in AAP and PS2APP mice by peak 3. Mixed populations of two months old APP and PS2APP mice were treated for 2, 6, 24, 48 or 72 h with peak 3 (50 μg/kg i.p.). Subsequently, APP, C99, Abeta and actin levels were evaluated and ratios calculated as described. Data are expressed as % of untreated controls and represent means±SEM (n=10-15). A, Abeta/APP and B, C99/Abeta ratios at 6, 24 and 48 h after injection (*, $p<0.05$; , $p<0.01$; *, $p<0.001$ vs. untreated control).

At 6 h after i.p. injection, 50 µg/kg peak 3 exerted a significant effect in reduction of brain Abeta levels. To test how long this effect is maintained we analyzed brain extracts from PS2APP mice treated for 2, 6, 24, 48 and 72 h with 50 µg/kg peak 3. No significant changes either in APP/Actin or C99/APP ratios were observed over the whole time period. In contrast, Abeta/APP levels were significantly reduced at 6, 24 and 48 h after i.p. injection ($p<0.05$, $p<0.001$ and $p<0.01$, respectively) indicating an Abeta lowering effect of peak 3 over at least 48 h (FIG. 10A). C99/Abeta ratios, representing Abeta clearance independent of Abeta production (since C99/APP remained constant), were significantly increased in a very similar time course being well maintained over at least 24 h after injection (FIG. 10B). Taken together, these data demonstrate that peak 3 is able to reduce brain Abeta in PS2APP.

Example 11

Binding to IGF Binding Proteins IGFBP4 (BP4) and IGFBP5 (BP5)

IGFBP4 (SwissProt 22692) was identified and cloned by Shimasaki, S., Mol. Endocrinol. 4 (1990) 1451-1458. IGFBP5 (SwissProt 24593) was identified and cloned by Kiefer, M. C., Biochem. Biophys. Res. Commun. 176 (1991) 219-225. Both binding proteins were produced recombinantly in E. coli.

For Surface Plasmon Resonance (SPR) analysis of the protein interaction a Biacore 3000 instrument was used. Running and reaction buffer was HBS-P (10 mM HEPES, 150 mM NaCl, 0.005% polysurfactant, ph 7.4) at 25° C. All samples were pre-cooled at 12° C. IGFBP4 and IGFBP5 were amine-coupled at concentrations of 5 µg/ml. The coupling on a CM5 chip resulted in a loading signal of ~700 RUs. Pegylated IGF-I samples (analytes) were injected at 5 concentrations between 1.23 nM and 100 nM for 5 minutes (association phase) and washed with HBS-P for five minutes at a flow rate of 50 µl/min. The chip surface was regenerated by one injection of 100 mM HCl for 1 min.

The chip, assay format and sequence of injections correspond to the description in table 2. Data evaluation was done by using a 1:1 Langmuir binding model,

TABLE 2

| Chip | Ligand | Analyte | ka (1/Ms) | kd (1/s) | KD (M) |
|---|---|---|---|---|---|
| CM5 | BP4 | IGF-1 | $4.0 \times 10^6$ | $7.2 \times 10^{-4}$ | $1.8 \times 10^{-10}$ |
| CM5 | BP4 | 40 kDa/NT-RRRK | $5.4 \times 10^4$ | $1.5 \times 10^{-3}$ | $2.8 \times 10^{-8}$ |
| CM5 | BP4 | 40 kDa/RRRK | $7.1 \times 10^4$ | $6.8 \times 10^{-4}$ | $9.5 \times 10^{-9}$ |

TABLE 2-continued

| Chip | Ligand | Analyte | ka (1/Ms) | kd (1/s) | KD (M) |
|---|---|---|---|---|---|
| CM5 | BP4 | composition | $6.9 \times 10^4$ | $5.3 \times 10^{-4}$ | $7.7 \times 10^{-9}$ |
| CM5 | BP5 | IGF-1 | $9.6 \times 10^6$ | $1.6 \times 10^{-3}$ | $1.7 \times 10^{-10}$ |
| CM5 | BP5 | 40 kDa/NT-RRRK | $1.1 \times 10^5$ | $2.1 \times 10^{-3}$ | $2.0 \times 10^{-8}$ |
| CM5 | BP5 | 40 kDa/RRRK | $1.5 \times 10^5$ | $2.0 \times 10^{-3}$ | $1.3 \times 10^{-8}$ |
| CM5 | BP5 | composition | $1.1 \times 10^5$ | $2.5 \times 10^{-3}$ | $2.3 \times 10^{-8}$ |

ABBREVIATIONS 40 kDa: 40 kDa PEG branched
40 kDa/NT-RRRK: RRRK which is N-terminally PEGylated with 40 kDa PEG
40 kDa/RRRK:RRRK which is lysine PEGylated at K68 with 40 kDa PEG
composition: composition of 40 kDa/NT-RRRK and 40 kDa/RRRK (1:1)

These results show, that all PEGylated IGF samples were actively binding to IGFBP4 and IGFBP5 in a similar range. All pegylated samples showed a significantly reduced association rate constant in comparison to non-PEGylated IGF.

Negative control data (e.g. buffer curves) were subtracted from sample curves for correction of system intrinsic baseline drift and for signal noise reduction.

Example 12

Autophosphorylation of IGF-IR by Ligands

In order to determine the ability of the polypeptides of the invention to activate IGF-IR and induce IGF-IR phosphorylation, IGF-IR overexpressing cells were stimulated by the polypeptides of the invention and IGF-IR phosphorylation status was analyzed subsequently by ELISA.

For ELISA, 96-Well streptavidin coated polystyrene plates (Nunc) were coated with 100 µl monoclonal antibody against human IGF-1Rα (0.5 mg/ml) diluted 1:350 in PBST with 3% BSA. After incubation for 1 hour at room temperature on a plate shaker, the coating solution was removed and plates were washed thrice with 200 µl PBST per well.

IGF-IR transfected NIH-3T3 cells were plated in MEM Dulbecco medium (DMEM) with high glucose (PAA, CatNo. E15-009) supplemented with 2 mM L-Glutamin (Gibco, CatNo. 25030-024) and 0.5% heat inactivated FCS (PAA, CatNo. A15-771). For determination of $EC_{50}$ values, 96 well plates inoculated with $1.3*10^4$ cells per well were cultivated for two days at 37° C. and 5% $CO_2$.

After 48 hours of cultivation with low serum medium, the medium was carefully removed and replaced by different concentrations of the polypeptides of the invention diluted in 50 µl of the respective medium. After 10 minutes of incubation at 37° C. and 5% $CO_2$ the medium was carefully removed by aspiration and 120 µl of cold lysis buffer was added per well (50 mM Tris pH 7.5, 1 mM EDTA, 1 mM EGTA, 20% glycerol, 1% Triton-X100, 100 mM NaF, 1 mM $NaVO_4$, Complete™ protease inhibitor). The plates were incubated with lysis buffer for 15 minutes at 4° C. on a plate shaker and 100 µl of the well contents were transferred afterwards to the ELISA plates coated with monoclonal antibody against human IGF-1Rα. The lysates were incubated for 1 h at room temperature on a plate shaker to allow IGF-IR binding to the capture antibody and were carefully aspirated afterwards. Unbound material was removed by three washing steps with 200 µl PBST/well each.

To detect the bound phosphorylated IGF-1R, 100 µl of polyclonal IgG rabbit antibody against human IGF-1Rα diluted 1:12650 in 3% BSA/PBST were added to each well followed by another incubation period for 1 hour at room temperature on the plate shaker. The well contents were again carefully removed and the wells washed three times with 200 µl PBST/well. For the detection of polyclonal rabbit antibody, 100 µl of a polyclonal antibody against rabbit IgG coupled to HRP (Cell Signaling Technology Inc. USA) diluted 1:6000 in 3% BSA/PBST were added to each well. After incubation for 1 hour at room temperature on a shaker, unbound detection antibody was removed by washing the plates six times with 200 µl PBST/well. As a substrate for the antibody-coupled HRP, 100 d of 3,3'-5,5'-tetramethylbenzidine were added to each well followed by another incubation for 0.5 hours at room temperature on a shaker.

Quantification occurred after stopping the reaction with 25 µl/well 1M $H_2SO_4$ by measuring absorption at a wavelength of 450 nm.

The obtained OD450 values of the samples were transformed into percent activation using 10 nM IGF-1 as 100% (max) and w/o IGF-1 as 0% (min) controls by the following formula: percent activation=(sample−min)/(max−min). The resulting EC50 (polypeptide concentrations at half maximum activation of IGF-1R) values are summarized in table 3.

TABLE 3

| Sample | EC50 [nM] | "STDEV" |
| --- | --- | --- |
| K68-RRRK 20 kDa linear | 2.1 | 0.2 |
| NT-RRRK 20 kDa linear | 29.6 | 1.9 |
| composition 20 kDa linear | 7.6 | |
| K68-RRRK 30 kDa linear | 4.7 | 0.9 |
| NT-RRRK 30 kDa linear | 44.5 | 5.0 |
| composition 30 kDa linear | 9.2 | 1.1 |
| composition 40 kD branched | 16.4 | 0.7 |
| K68-RRRK 20 kD branched | 1.5 | 1.1 |
| composition 20 kD branched | 5.1 | 0.5 |
| NT-RRRK 40 kD branched | 19.9 | 1.1 |

Abbreviations are as in example 11.

What is claimed:

1. A conjugate comprising an IGF-I (insulin-like growth factor I) variant and poly(ethylene glycol), wherein the IGF-I variant has amino acid alterations from wild-type IGF-I at positions 27 and 65 or at positions 27 and 68, and the amino acid alterations do not reduce in vitro binding affinity for an IGF-I binding protein and in vitro IGF-I receptor phosphorylation; wherein the IGF-I variant selected from the group consisting of R27, R37, R65, K68 (RRRK) and R27, R37, K65, R68 (RRKR) and wherein the poly(ethylene glycol) is conjugated to the IGF-1 variant via a lysine primary amino group without poly(ethylene glycol) being conjugated to the N-terminus of the IGF-I variant.

2. The conjugate according to claim 1 wherein the poly(ethylene glycol) has an overall molecular weight of from 20 to 100 kDa.

3. The conjugate according to claim 1 wherein the IGF-I variant is RRRK and conjugated to poly(ethylene glycol) at K68.

4. The conjugate according to claim 1 wherein up to three amino acids at the N-terminus are truncated.

5. The conjugate according to claim 1 wherein the poly(ethylene glycol) is branched.

6. A pharmaceutical composition comprising the conjugate of claim 1 and a pharmaceutically acceptable carrier.

* * * * *